(12) United States Patent
Zimenkov et al.

(10) Patent No.: US 10,072,982 B2
(45) Date of Patent: *Sep. 11, 2018

(54) UNIVERSAL MULTIDETECTION SYSTEM FOR MICROPLATES

(71) Applicant: BIOTEK INSTRUMENTS, INC., Winooski, VT (US)

(72) Inventors: Oleg Zimenkov, South Burlington, VT (US); Xavier Amouretti, Essex Junction, VT (US); Michael Kontorovich, Colchester, VT (US); Ben Norris, Monkton, VT (US); Richard N. Sears, Jericho, VT (US); Dan J. Venditti, Jr., Colchester, VT (US); Christopher Many, Highgate, VT (US); Bill Anderson, Westford, VT (US); Ben Knight, Burlington, VT (US); James Piette, Winooski, VT (US); Ross Piette, Essex, VT (US); Joe Tobey, Essex, VT (US); Brian Ferris, Georgia, VT (US)

(73) Assignee: BIOTEK INSTRUMENTS, INC., Winooski, VT (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/390,128

(22) Filed: Dec. 23, 2016

(65) Prior Publication Data
US 2017/0108438 A1    Apr. 20, 2017

Related U.S. Application Data

(60) Continuation of application No. 13/485,446, filed on May 31, 2012, now Pat. No. 9,557,217, which is a (Continued)

(51) Int. Cl.
*G01J 3/42* (2006.01)
*G01J 3/02* (2006.01)
(Continued)

(52) U.S. Cl.
CPC ............. *G01J 3/42* (2013.01); *G01J 3/027* (2013.01); *G01J 3/0264* (2013.01);
(Continued)

(58) Field of Classification Search
CPC .......... G01J 3/0224; G01J 3/0294; G01J 3/10; G01J 3/42; G01J 3/4406; G01J 3/443;
(Continued)

(56) References Cited

U.S. PATENT DOCUMENTS 3,843,257 A   10/1974  Wooten
3,999,864 A   12/1976  Mutter
(Continued)

FOREIGN PATENT DOCUMENTS

DE   199 16 748 A1   10/2000
DE   102 36 029 A1    2/2004
(Continued)

OTHER PUBLICATIONS

EPO Communication in European application (EP 08 729 602.6), forwarding thirdpart observations, dated Oct. 2, 2011.
(Continued)

*Primary Examiner* — Gordon J Stock, Jr.
(74) *Attorney, Agent, or Firm* — Sughrue Mion, PLLC

(57) ABSTRACT

An apparatus for optically analyzing a sample may include an imaging subsystem that images the sample, one or more analyzing subsystems that analyze the sample, a temperature control subsystem that controls a temperature of the atmosphere within the apparatus, a gas control subsystem that controls a composition of the atmosphere within the apparatus, and a control module that controls the various subsystems of the apparatus.

18 Claims, 30 Drawing Sheets

Related U.S. Application Data continuation-in-part of application No. 12/838,804, filed on Jul. 19, 2010, now Pat. No. 8,218,141, which is a division of application No. 11/802,831, filed on May 25, 2007, now Pat. No. 7,782,454.

(60) Provisional application No. 60/900,976, filed on Feb. 13, 2007.

(51) Int. Cl.

| | | |
|---|---|---|
| *G01J 3/44* | (2006.01) | |
| *G01J 3/443* | (2006.01) | |
| *G01N 21/64* | (2006.01) | |
| *G01N 21/76* | (2006.01) | |
| *G01J 3/10* | (2006.01) | |

(52) U.S. Cl.
CPC ............ *G01J 3/0291* (2013.01); *G01J 3/443* (2013.01); *G01J 3/4406* (2013.01); *G01N 21/64* (2013.01); *G01N 21/6447* (2013.01); *G01N 21/6452* (2013.01); *G01N 21/6456* (2013.01); *G01N 21/76* (2013.01); *G01J 3/0218* (2013.01); *G01J 3/0224* (2013.01); *G01J 3/0235* (2013.01); *G01J 3/0294* (2013.01); *G01J 3/10* (2013.01)

(58) Field of Classification Search
CPC ...... G01J 3/0218; G01J 3/0235; G01J 3/0264; G01J 3/027; G01J 3/0291; G01J 3/28; G01J 3/2803; G01J 3/2823; G01J 2003/2806; G01J 2003/2813; G01J 2003/2816; G01J 2003/282; G01J 2003/2826; G01N 2021/6463; G01N 2021/6417; G01N 2021/6419; G01N 2021/6421; G01N 21/6452; G01N 21/76; G01N 21/6456; G01N 21/645; G01N 21/763; G01N 21/64; G01N 21/6447

See application file for complete search history.

(56) References Cited

U.S. PATENT DOCUMENTS

| | | | |
|---|---|---|---|
| 4,516,856 A | 5/1985 | Popelka | |
| 4,531,834 A | 7/1985 | Nogami | |
| 4,669,878 A | 6/1987 | Meier | |
| 4,730,922 A | 3/1988 | Bach et al. | |
| 4,795,256 A | 1/1989 | Krause et al. | |
| 5,290,513 A | 3/1994 | Berthold et al. | |
| 5,383,023 A | 1/1995 | Walleczek | |
| 5,784,152 A | 7/1998 | Heffelfinger et al. | |
| 5,933,232 A | 8/1999 | Atzler et al. | |
| 6,025,985 A | 2/2000 | Leytes et al. | |
| 6,042,785 A | 3/2000 | Harju | |
| 6,071,748 A | 6/2000 | Modlin et al. | |
| 6,097,025 A | 8/2000 | Modlin et al. | |
| 6,144,455 A | 11/2000 | Tuunanen et al. | |
| 6,187,267 B1 | 2/2001 | Taylor et al. | |
| 6,232,608 B1 | 5/2001 | Giebeler et al. | |
| 6,236,456 B1 | 5/2001 | Giebeler et al. | |
| 6,307,626 B1 | 10/2001 | Miles et al. | |
| 6,313,471 B1 | 11/2001 | Giebeler et al. | |
| 6,316,774 B1 | 11/2001 | Giebeler et al. | |
| 6,466,316 B2 | 10/2002 | Modlin et al. | |
| 6,469,311 B1 | 10/2002 | Modlin et al. | |
| 6,538,735 B1 | 3/2003 | Duebendorfer et al. | |
| 6,563,581 B1 | 5/2003 | Oldham et al. | |
| 6,654,119 B1 | 11/2003 | Gould et al. | |
| 6,671,624 B1 | 12/2003 | Dunlay et al. | |
| 6,673,595 B2 | 1/2004 | Barbera-Guillem | |
| 6,730,901 B1 | 5/2004 | Rushbrooke et al. | |
| 6,756,207 B1 | 6/2004 | Giuliano et al. | |
| 6,822,741 B2 | 11/2004 | Aronkyto et al. | |
| 6,825,921 B1 | 11/2004 | Modlin et al. | |
| 6,965,105 B2 | 11/2005 | Oldham et al. | |
| 6,982,434 B2 | 1/2006 | Smith et al. | |
| 6,985,225 B2 | 1/2006 | Bechem et al. | |
| 7,352,459 B2 | 4/2008 | Gould et al. | |
| 7,782,454 B2 | 8/2010 | Zimenkov et al. | |
| 8,218,141 B2 * | 7/2012 | Zimenkov | G01J 3/10 356/301 |
| 8,748,165 B2 * | 6/2014 | Vangbo | G01N 27/44791 422/50 |
| 9,012,236 B2 * | 4/2015 | Jovanovich | G01N 35/00029 422/502 |
| 9,188,527 B2 * | 11/2015 | Atzler | G01N 21/31 |
| 9,557,217 B2 * | 1/2017 | Zimenkov | G01J 3/10 |
| 2002/0009391 A1 | 1/2002 | Marquiss et al. | |
| 2002/0043626 A1 | 4/2002 | Booker et al. | |
| 2002/0070349 A1 | 6/2002 | Hoyt | |
| 2002/0090320 A1 | 7/2002 | Burow et al. | |
| 2002/0155507 A1 * | 10/2002 | Bruchez | B82Y 15/00 435/7.2 |
| 2003/0030797 A1 | 2/2003 | Palladino et al. | |
| 2003/0042428 A1 | 3/2003 | Peukert et al. | |
| 2003/0103662 A1 | 6/2003 | Finkbeiner | |
| 2003/0127609 A1 | 7/2003 | El-Hage et al. | |
| 2003/0219754 A1 | 11/2003 | Olesky et al. | |
| 2004/0057870 A1 | 3/2004 | Isaksson et al. | |
| 2004/0113095 A1 | 6/2004 | Peltie et al. | |
| 2004/0200979 A1 | 10/2004 | Reel | |
| 2004/0202577 A1 | 10/2004 | McNeil et al. | |
| 2005/0012929 A1 | 1/2005 | Booker et al. | |
| 2005/0046849 A1 | 3/2005 | Cromwell et al. | |
| 2005/0051723 A1 | 3/2005 | Neagle et al. | |
| 2005/0052646 A1 | 3/2005 | Wohlstadter et al. | |
| 2005/0062969 A1 | 3/2005 | Harju et al. | |
| 2005/0105080 A1 | 5/2005 | Landlinger | |
| 2005/0112783 A1 | 5/2005 | Evans et al. | |
| 2005/0118060 A1 | 6/2005 | Evans et al. | |
| 2005/0157299 A1 | 7/2005 | Heffelfinger | |
| 2005/0196325 A1 | 9/2005 | Bathe et al. | |
| 2005/0213374 A1 | 9/2005 | Xu et al. | |
| 2005/0218338 A1 | 10/2005 | Wulf et al. | |
| 2006/0066857 A1 | 3/2006 | Ok et al. | |
| 2006/0094868 A1 | 5/2006 | Giuliano et al. | |
| 2006/0257999 A1 | 11/2006 | Chang et al. | |
| 2007/0009396 A1 | 1/2007 | Ho | |
| 2007/0121199 A1 | 5/2007 | Suzuki et al. | |
| 2007/0177149 A1 * | 8/2007 | Aronkyto | G01N 21/6428 356/417 |
| 2007/0231217 A1 | 10/2007 | Clinton et al. | |
| 2007/0248494 A1 * | 10/2007 | Mokelke | G01N 35/028 422/82.08 |
| 2008/0212866 A1 | 9/2008 | Lett et al. | |
| 2009/0208072 A1 | 8/2009 | Seibel et al. | |
| 2011/0051235 A1 | 3/2011 | Miteva et al. | |
| 2011/0216953 A1 | 9/2011 | Callahan et al. | |
| 2012/0034569 A1 | 2/2012 | Sakamoto et al. | |
| 2012/0046203 A1 | 2/2012 | Walsh et al. | |
| 2012/0064564 A1 | 3/2012 | Grassl et al. | |
| 2012/0153188 A1 | 6/2012 | Barrett | |
| 2012/0300194 A1 | 11/2012 | Zimenkov et al. | |
| 2013/0078624 A1 * | 3/2013 | Holmes | C12Q 1/00 435/6.11 |
| 2013/0224877 A1 | 8/2013 | Phillips et al. | |
| 2013/0280748 A1 | 10/2013 | Gebetsroither et al. | |
| 2016/0320381 A1 * | 11/2016 | Holmes | G01N 33/54386 |
| 2016/0325284 A1 * | 11/2016 | Camillo | B01L 3/5027 |

FOREIGN PATENT DOCUMENTS

| | | |
|---|---|---|
| DE | 10 2009 018 325 A1 | 11/2010 |
| EP | 2 253 983 A2 | 11/2010 |
| GB | 1 396 806 | 6/1975 |
| IT | MI912510 A1 | 3/1993 |
| JP | 58062542 A | 4/1983 |
| JP | 11037923 A | 2/1999 |
| WO | 99/39184 A1 | 8/1999 |
| WO | 0017643 | 3/2000 |
| WO | 2004/069409 A2 | 8/2004 |

(56) References Cited

FOREIGN PATENT DOCUMENTS

| WO | 2005/016527 | A2 | 2/2005 |
| WO | 2006/031537 | A2 | 3/2006 |
| WO | 2008/117031 | A1 | 10/2008 |

OTHER PUBLICATIONS

Joseph R. Lakowicz: Principles of Fluorescence Spectroscopy; 3rd edition 2006; p. 29.
McPherson: Optimized Fluorescence Detection; Fluorescence Detectors; http://www.mcphersoninc.com/hplcdetectors/optimze.htm.
Robert H. Christenson, et al., Standardization of Creatine Kinase-MB (CK-MB) Mass Assays: The Use of Recombinant CK-MB as a Reference Material; Abused Drugs III; Clinical Chemistry 45: 1414-1423, 1999; http://www.clinchem.org/cgi/content/full/45/9/1414.
Extended European Search Report issued in EP Application No. 08729602.6 dated Nov. 6, 2013.
Supplementary European search Report dated Mar. 1, 2016, in counterpart European Application No. EP 13 79 7139.

\* cited by examiner

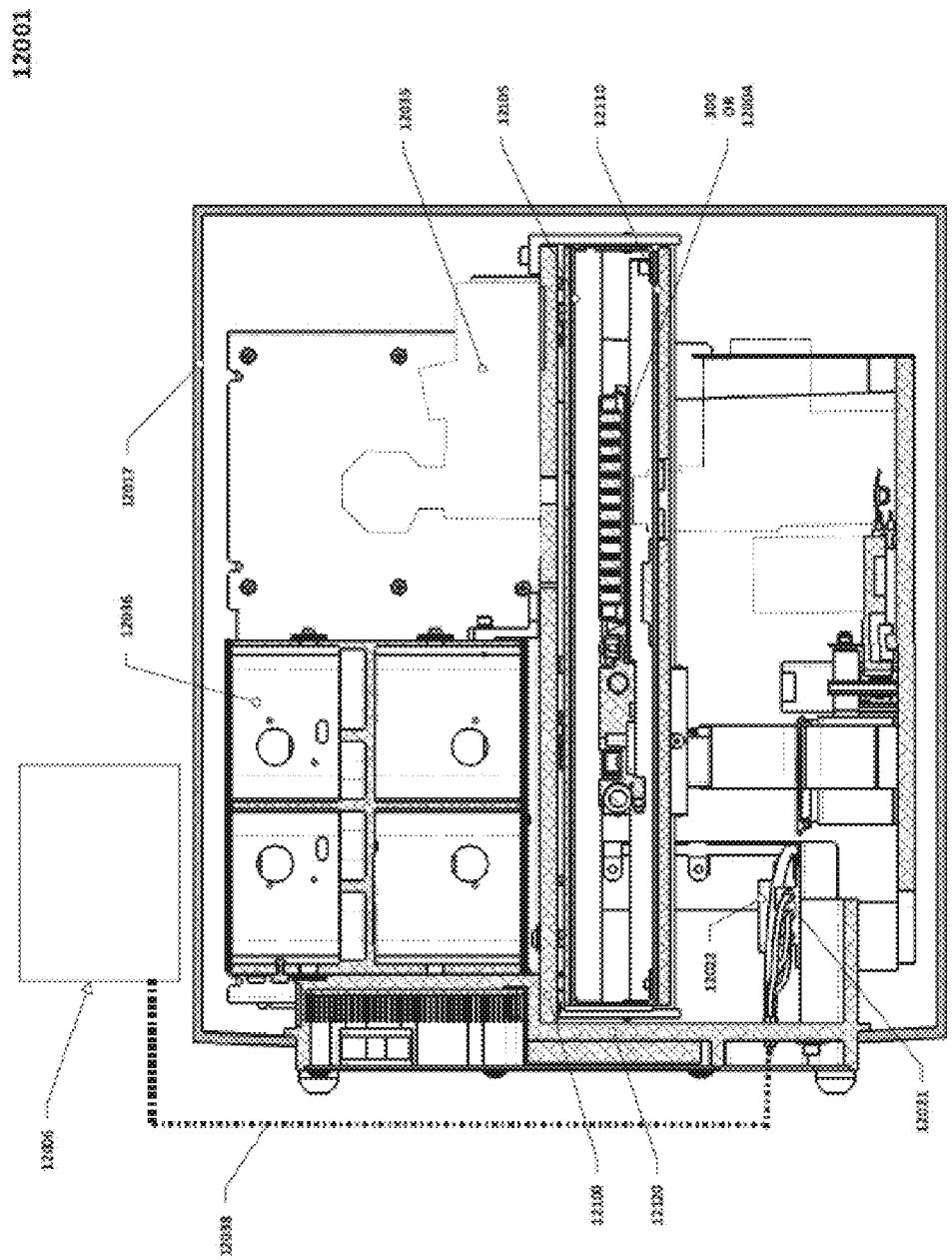

FIG. 27

UNIVERSAL MULTIDETECTION SYSTEM FOR MICROPLATES

CROSS-REFERENCE TO RELATED APPLICATION

This application is a continuation of U.S. application Ser. No. 13/485,446 filed on May 31, 2012, which is a continuation-in-part of U.S. application Ser. No. 12/838,804 filed on Jul. 19, 2010, now U.S. Pat. No. 8,218,141 issued Jul. 10, 2012, which is a divisional of U.S. application Ser. No. 11/802,831, filed May 25, 2007, which issued as U.S. Pat. No. 7,782,454, the disclosures of which are incorporated by reference in their entireties.

BACKGROUND

1. Field

Apparatuses and methods consistent with the present invention relate to detection systems, including the detection of fluorescence, absorbance, and chemiluminescence in samples placed in the wells of microplates.

2. Description of the Related Work

Multiple analytical instruments are used in laboratories to evaluate samples under test that are placed into vessels of various shapes. In the past twenty years, a microplate format has become very popular, as it lends itself to testing many samples on a single matrix-style receptacle. The first detection systems for microplates were absorbance readers. Later dedicated fluorometers were developed, followed by instruments to measure chemiluminescence.

The range of assay chemistries and labeling technologies continues to grow. Currently employed detection methods include absorbance, multiplexed fluorescence and chemiluminescence, fluorescence polarization (FP), time-resolved fluorescence (TRF), fluorescence resonance energy transfer (FRET), quenching methods, and specially designed labels with intensity and spectral responsiveness to environmental conditions. Along with this range of detection methods, users are conjugating an ever-growing array of organic and inorganic labels for targets, ranging from small-molecule drug candidates to proteins and nucleic acids, and to subcellular structures and cells.

FIG. 1 illustrates the general structure of a related art multimode detection system. As shown in FIG. 1, a typical system comprises a light source 10, an excitation spectral device 20, an optical module 30, a measurement chamber 60 with samples 70, an emission spectral device 40, and a detector 50. There are two distinct types of related art multimode detection systems: filter-based units and monochromator-based units.

Filter-based units, when offered with high quality filters in combination with dichroic mirrors, allow for measurements with very low detection limits. This is mainly due to a high signal level, which is achieved with the filters, in combination with a high signal-to-noise ratio, which is achieved by a high level of blocking of the unwanted radiation around the desired waveband. The transmittance of filters is routinely over 50%, and this high level of transmittance can be achieved independent of the wavelength. Therefore, a very broad spectral range can be covered equally well from the deep ultraviolet (UV) to the infrared (IR), and the bandpass of the filter can be tailored to the specific application.

However, the filter-based unit cannot obtain a spectral scan for excitation or emission of the substance under investigation. A user must know upfront what substance he or she is working with and order an appropriate filter set. In addition, when working in the deep UV, filters tend to degrade when exposed to the UV radiation of the light source, due to solarization. Also, maintaining libraries of filters for the full range of labels is prohibitively expensive, and appropriate combinations are often not readily available for a given label, conjugation chemistry, target molecule, and assay condition. Further, the effects of these conditions are not always predictable based on the nominal spectra of the basic label.

Monochromator-based instruments offer a high level of flexibility in terms of choosing the wavelengths and obtaining scans of excitation and emission spectra, thus allowing the user to work with unknown substances. This also permits optimization of the measurements for perturbations to the spectra of labels due to assay conditions, conjugation chemistries, and target molecules. Additionally, when working with real biological or biochemical samples, interfering signals from other sample components may require optimization of excitation and emission wavelengths for the exact assay conditions.

The monochromators used in modern instruments are usually based on diffraction gratings, and use a flat grating for dispersion and concave mirrors for focusing light, or concave gratings that combine dispersive and focusing functions. Monochromators require order sorting filters to separate high spectral orders, but in the range from 200 nm to about 380 nm, no order sorting filters are needed. Therefore, there is no need for filters that withstand UV radiation, and the solarization problem is avoided.

However, the response of the monochromator is not constant across the wavelength range. One can obtain a system with a good signal in the UV, the visible, or the IR; however, one cannot obtain a system with a good signal in all of the wavelength ranges in the same monochromator-based unit. A usual compromise is to optimize the excitation monochromator in the UV and to optimize the emission monochromator in the visible or IR, because the wavelength of the emission light shifts to the right with respect to the wavelength of the excitation light.

In order to obtain low detection limits, the monochromator must have very low stray light. A traditional way to achieve this in the monochromator-based system is to employ two stage monochromators. These are called double monochromators, and contain two single monochromators placed in series. While this does result in very low stray light, the penalty is a dramatic decrease in signal, especially in spectral regions where the response of the single stage monochromator is already low. There are several instruments in the field based on this method.

In terms of performance, the filter-based units achieve significantly lower detection limits in fluorescence intensity applications across the full spectral range, and work significantly better with techniques such as TRF, FP, and Homogeneous Time-Resolved Fluorescence (HTRF), all of which require the strong signal provided by the filter-based units. On the other hand, the monochromator-based units provide the flexibility of choosing any wavelength and the ability to obtain a spectral scan, at the expense of lower sensitivity.

U.S. Pat. No. 6,313,471 describes a method that combines bandpass filters and monochromators in series in a detection system. In this method, the bandpass filter acts as a crude first stage monochromator. The instrument splits the full spectral range of interest into several regions corresponding to the number of filters employed, and blocks radiation from adjacent regions by using additional filters. The single stage monochromator that follows the bandpass filters then selects the wavelength of interest from this prefiltered range.

However, with a limited number of prefiltered regions, this method is limited in flexibility. If both the excitation and emission wavelengths fall into one region, the method is not effective in achieving low stray light or high performance. True spectral scanning is not readily accomplished with this method. This limits its utility for spectral measurement and optimization under conditions of fine spectral perturbation.

A most recent advance in microplate instrumentation is a multi-detection analyzer. An example of this product is the Synergy line from BioTek Instruments. The included modalities are absorbance, fluorescence, luminescence, and fluid injection.

There is a desire to study cellular processes in microplates, and thus the need to visually study the contents of the microwells. Accordingly, a synergistic effect would be obtained by combining in one instrument the ability to perform imaging of the wells of the microplates and reading modality, such as absorbance, luminescence, or high sensitivity fluorescence readings.

SUMMARY

Exemplary embodiments described herein overcome the above disadvantages and other disadvantages not described above. Also, the exemplary embodiments are not required to overcome the disadvantages described above, and an exemplary embodiment may not overcome any of the problems described above.

According to an aspect of an exemplary embodiment, there is provided a device for analyzing one or more samples, the device including a support for a receptacle that holds a sample; an imaging subsystem that images the sample; and an analyzing subsystem that analyzes the sample.

According to an aspect of an exemplary embodiment, there is provided a sample analysis method including selecting at least one subsystem from among a plurality of subsystems of a sample analysis device that examines one or more samples, the plurality of subsystems comprising an imaging subsystem that images the one or more samples and an analyzing subsystem that analyzes the one or more samples; and controlling the selected at least one subsystem to perform an examination on the one or more samples, the examination comprising an imaging operation of the imaging subsystem that images the one or more samples and an analyzing operation of the analyzing subsystem that analyzes the one or more samples.

According to an aspect of an exemplary embodiment, there is provided a non-transitory computer-readable medium having embodied thereon a program which when executed by a computer causes the computer to execute a sample examination method, the method including selecting at least one subsystem from among a plurality of subsystems of a sample analysis device that examines one or more samples, the plurality of subsystems comprising an imaging subsystem that images the one or more samples and an analyzing subsystem that analyzes the one or more samples; and controlling the selected at least one subsystem to perform an examination on the one or more samples, the examination comprising an imaging operation of the imaging subsystem that images the one or more samples and an analyzing operation of the analyzing subsystem that analyzes the one or more samples.

BRIEF DESCRIPTION OF THE DRAWINGS

The above and other aspects will become more apparent by describing in detail exemplary embodiments thereof with reference to the attached drawings, in which:

FIGS. 12 and 13 illustrate a UMS according to an exemplary embodiment, in which atmospheric control is implemented.

FIG. 27 illustrates results of operations of an analysis subsystem and an imaging subsystem of a UMS, according to an exemplary embodiment.

DETAILED DESCRIPTION OF EXEMPLARY EMBODIMENTS

Figure 1:
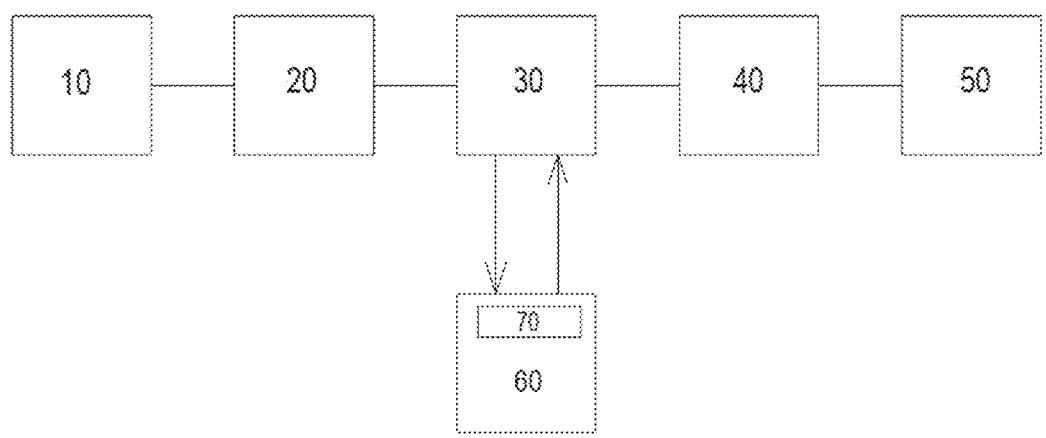
FIG. 1 illustrates a general structure of a multimode detection system.

Cell-based and live-cell assays are becoming more and more popular in life science research and drug discovery as the field of biology keeps developing in depth and complexity. Cells are complex biological entities and multi-parametric, multiplexed assays are becoming more common (for example, assay measuring 3 cellular events in parallel). The ability to monitor live cells using multi-parametric assays is key to developing a better understanding of cell biology.

Assays may be conducted with microplate multimode readers, using filters or monochromators, which collect as much signal as possible from the microplate well using the full population of cells. These assays are typically quantitative and the signal is an average produced by the full population of cells. Other assays use microplate imaging readers that contain microscope objectives and a camera to image a small portion of the well and thus a sub-population of cells. This provides the ability to localize where the signal is originating in individual cells and provide semi-quantitative information from the extent of the signal compared to controls. Another way of differentiating these assays is whether they involve end-point or kinetic responses.

One benefit of a hybrid instrument is to dramatically increase the ability to get multi-parametric data from live-cell assays. In particular, this novel instrument design allows making population-based detection synchronous with single-cell results available from imaging. 2D imaging information produces feedback about individual cell behaviors within the population. This allows the simultaneous study of populations and single cells, which will identify sub-populations and better characterize the biology and drug effects.

This important benefit is especially evident in the case of kinetic assays. Cellular events occur over a certain period of time (minutes, hours or days depending on type of event) and kinetic monitoring allows recording changes over time. Only a hybrid system as described herein will allow monitoring in parallel population-based information with the microplate reader optics and single cell-based information with the imaging optics, providing a very detailed view of what is happening in the sample. Such an assay may be one in which cell viability and cell death are measured. This assay is typically measured with standard plate readers and the instrument acquires a signal coming from the solution in which the cells grow. Such a signal cannot be satisfactorily measured using imaging optics. On the other hand, these indirect signals are assumed to correspond to cell death and cell viability events but only direct visual inspection can confirm what is happening at the cellular level. Monitoring both chemical signals in solution with the plate reader optics and actual cell morphology changes with the imaging optics enhances the quality of the data set and provide more information on the actual cellular events.

Another unique benefit of a hybrid microplate reader defined as both a microplate multimode reader and microplate imaging reader is significant instrumentation cost savings and workflow improvement. This is due to the ability to automatically perform both end-point and kinetic assays on both sub- and full populations of cells in the same sample, during the same experiment. Normally, this would require at least two separate instruments. An example of this would be where a GFP fusion protein with Histone H3 is created using the Bacmam transfection technology. Histones are located exclusively in the cell nucleus, so imaging of sub-populations of cells using the imaging part of the hybrid reader is a useful validation step to ensure that green fluorescence from GFP is located exclusively in the nucleus. The determination of the extent of histone deacetylation at the lysine 9 residue of histone H3 is then conducted as an end-point assay using a labeled antibody against histone H3(lysine9) on the full population of cells in the well using the optics of a microplate multimode reader in the hybrid instrument.

Yet another unique benefit is the ability to improve on two major drawbacks of imaging: read speed and amount of data generated. Imaging takes longer than acquiring one data point per sample, and each individual sample file can be 1 MB or more. An instrument in accordance with aspects of the present application will allow quickly scanning dozens or hundreds of samples, identifying the samples of interest then limiting imaging to these identified samples. This process will significantly reduce the total acquisition time and as well as the final size of the data set.

The combination of an imaging subsystem and an analyzing subsystem permits benefits in many areas, including those already discussed and those discussed below.

a. Cell Counting

The purpose of cell counting in microplate assays is to estimate the increase or decrease of a cell population after treatment with a molecule of interest. Cytotoxicity assays are intended to measure population decline while cell proliferation assays are designed to detect population growth. These assays are among the most common cell-based microplate assays run in life-science laboratories. In conventional microplate readers, cell counting is performed using assays that generate a signal proportional to the number of cells. One of the most common such assay is a luminescent ATP assay: at the time of measurement, the cells are lysed (the cell membrane is destroyed so that the content of the cell is released), and ATP (energy-storage molecule found in all living cells) concentration is measured using a reagent that generates light in the presence of ATP. ATP concentration is proportional to the number of cells, and as a result the luminescent signal is proportional to the number of cells prior to analysis. Since this is a destructive assay, it can only be run once on each sample. There are instances where this type of assay can produce unexpected results.

The imaging subsystem permits scientists to take a quick look under a microscope before processing the microplate, to ensure that that cell population looks as expected. Accordingly, a second data point may be obtained for data analysis. Thus, for each sample, the user would have two sets of data: an image giving qualitative and semi-quantitative (estimate) information about the cell population, and a quantitative signal once the ATP assay has been run. The two sets of data would be expected to match in most cases (confirmation test), but a disagreement between the image and the quantitative assay would be a critical piece of information.

b. Transfection Efficiency and Gene Expression Assays

The combination of an imaging subsystem and an analyzing subsystem enables documenting the history of the cell population using one software and one instrument during transfection, which is a practice in modern laboratories to add genetic material to cells for the purpose of studying specific genes.

For example, once the transfection has been accomplished and cells have had time to recover from the process, the efficiency of the transfection step is estimated using the image subsystem to determine how many cells among the total cell population have effectively incorporated the new gene. Once this has been established, and if the transfection efficiency is high enough, researchers can then carry on with their experiments and will often run assays on conventional microplate readers.

c. Sample Documentation

The combination of an imaging subsystem and an analyzing subsystem enables sample information (qualitative and quantitative) to be regrouped in one electronic file, which will give researchers better and easier access to their sample data, allow researchers to easily see multi-dimensional data related to one sample, and thereby help bring clarity to the data-heavy cell-based research environment.

For example, large numbers of assay may rely on fluorescently labeled biological samples (cells, tissues, microscopic worms and fish, . . . ) to study the mechanisms of life. The imaging subsystem enables measuring data points on an entire population or organism by measuring the total fluorescence coming from a specific sample, which provides a quantitative answer. Further, qualitative data may be obtained to determine where fluorescence is located, whether the samples look as expected (number of cells, shape, distribution . . . ), etc., which permits better documentation of the sample.

The foregoing and other benefits attributable to the present application are particularly important for "Systems Biology", which is a concept at the core of modern biomedical research and has grown significantly since the year 2000. Systems Biology focuses on complex interactions in live biological systems, and relies heavily on a proper experimental model. The cell represents one of these models that is increasingly used to study and understand more complex Systems Biology questions that cannot be answered by simple mix-and-read assays. For this reason, proper instrumentation and software tools are essential for biologists running cell-based and live-cell assays.

When working on live cells, it is important to control gas levels, in particular $CO_2$ concentration for the purpose of maintaining close-to-physiological conditions. Cells being living organisms, they are sensitive to, and can react to, changes in their environment, such as changes in gas concentrations or changes in temperature conditions. Changes in the gas conditions and thus pH of growth media have even been linked to change in gene expression.

The ability of systems in accordance with aspects of the present application to maintain stable, continuous conditions while switching detection technology from imaging, to filter-based, to monochromator-based, allows monitoring multiple qualitative and quantitative cellular events while maintaining stable cell culture conditions. A benefit for users is the ability to precisely control and maintain optimal conditions on one instrument platform, instead of having to manually move samples from device to device, which could induce unexpected experimental artifacts (e.g. cells reacting to temperature change, mechanical movements or gas concentration changes while being transported from one device to the other).

Thus gas control in accordance with aspects of the present application will provide more reliable, physiologically relevant results in both short term and long term studies in which the same plate might be read many times over a time course. In this case the plate could remain in the instrument and not be subjected to multiple cycles of climate and gas changes.

Figure 2:
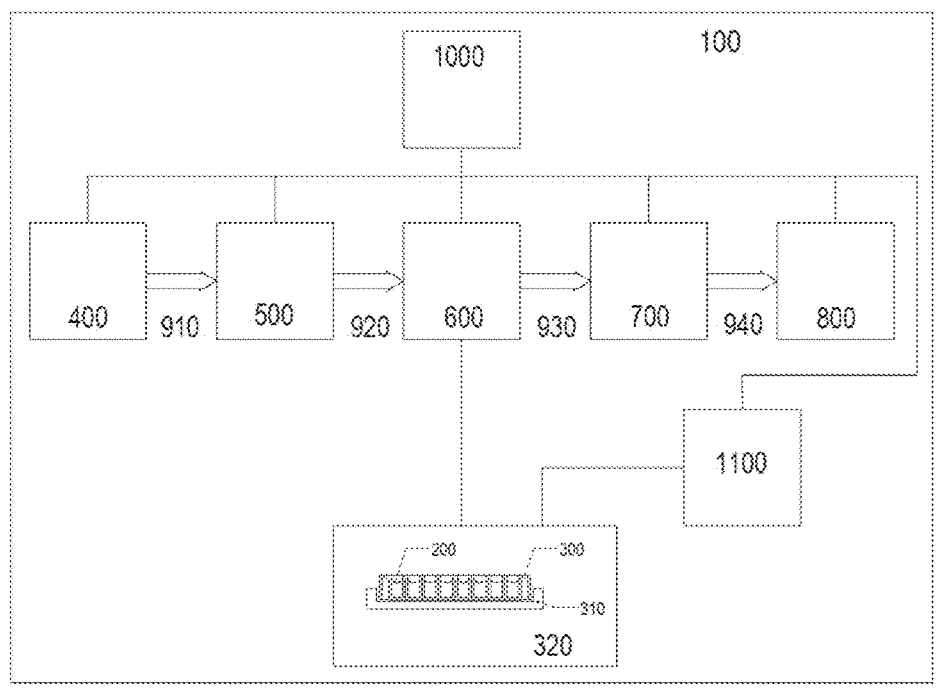
FIG. 2 illustrates certain components of a Universal Multi-detection System (UMS) according to an exemplary embodiment of the present invention.

FIG. 2 illustrates certain components of a Universal Multi-detection System (UMS) 100 according to an exemplary embodiment of the present invention. As shown in FIG. 2, samples are dispensed into the array of microwells 200 in the microplate 300. The microplate 300 is transported by the carriage 310 into the measurement chamber 320, which may be incubated, and is positioned sequentially for measurements. The light source 400 generates excitation light. The excitation spectral device 500 selects and transmits a narrow band of the excitation light. The waveband is typically between 5 and 40 nm wide. The excitation-emission separation device 600 directs the excitation light to the microwells 200, and then separates the emission light generated in the sample within the microwells 200 from the excitation light. The excitation-emission separation device 600 transmits the emission light to the emission spectral device 700, which transmits a narrow band of the emission light. The emission spectral device 700 should be configured to transmit as much emission light as possible, while blocking as much excitation light as possible and maximizing the signal-to-noise ratio. The detector 800 converts the emission light into an electrical signal. Although the light source 400, the excitation spectral device 500, the excitation-emission separation device 600, the emission spectral device 700, and the detector 800 are shown as separate modules, they can also be combined in a variety of ways.

As shown in FIG. 2, relay devices 910, 920, 930, and 940 provide optical connections between the light source 400, the excitation spectral device 500, the excitation-emission separation device 600, the emission spectral device 700, and the detector 800. The controller 1000 stores emission signals from samples in the microplate 300, analyzes the emission signals, computes parameters categorizing the optical measurements, and sends commands to the light source 400, the excitation spectral device 500, the excitation-emission separation device 600, the emission spectral device 700, or the detector 800. The commands can instruct the light source 400, the excitation spectral device 500, the excitation-emission separation device 600, the emission spectral device 700, or the detector 800 to change an internal parameter. For example, the commands can instruct the excitation spectral device 500 or the emission spectral device 700 to use one internal device instead of another internal device. Further, an optional dispenser 1100 delivers reagent to the microwells 200.

Figure 3:
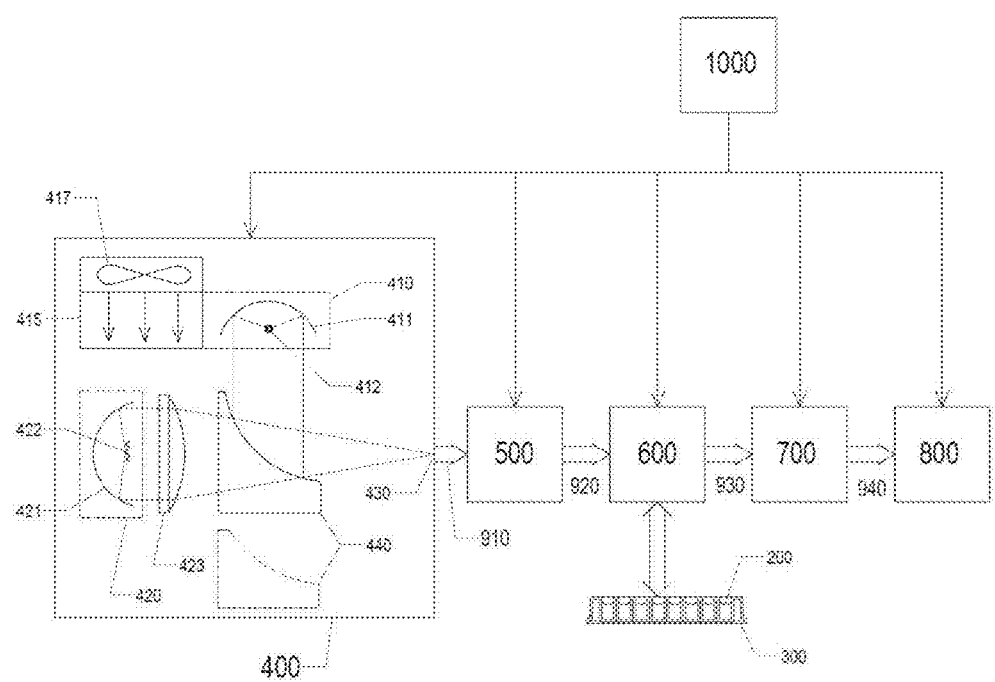
FIG. 3 illustrates a light source according to an exemplary embodiment of the present invention.

FIG. 3 illustrates the structure of the light source 400 according to an exemplary embodiment of the present invention. In a preferred embodiment, the light source 400 comprises only two light generating devices: a Xenon flash lamp 410 and a Tungsten lamp 420. In other embodiments the light source 400 may comprise a Xenon continuous wave lamp, a light emitting diode (LED), a laser, or any other light-generating device.

Tungsten sources are very stable, and their radiation extends from blue in the visible spectrum to the far IR, and peaks around 1 µm. They are most suitable for measurements in the visible and IR regions of the spectrum. In contrast, Xenon flash sources deliver most of their radiation in the deep UV, UV, and short visible spectral ranges. In addition, Xenon flash sources provide a very fast burst of light, lasting for several microseconds with a fast decay, and are therefore suitable for time resolved measurements in modern multi-detection systems.

Figure 5:
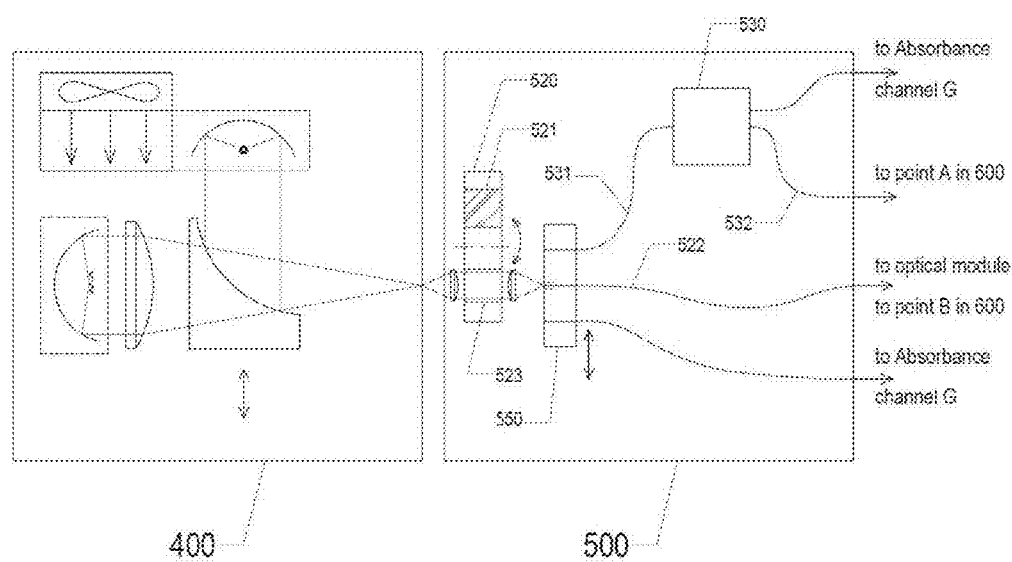
FIG. 5 shows optical connections between the light source, the excitation spectral device, and the excitation-emission separation device according to an exemplary embodiment of the present invention.

The Xenon flash lamp 410 has a parabolic reflector 411 positioned such that the arc 412 of the lamp 410 is located near the focal point of the reflector 411, providing an essentially collimated beam from the reflector 411. The Tungsten lamp 420 has a parabolic reflector 421 positioned such that the filament 422 of the lamp 420 is located near the focal point of the reflector 421, providing an essentially collimated beam from the reflector 421. FIG. 3 shows that a lens 423 may be used to focus the beam from the reflector 421 onto the exit portal 430 of the light source 400. As shown in FIG. 5, relay optics may be used to focus the beam onto the entrance of an optical fiber. Alternatively, the lens 423 may focus the beam from the reflector 421 directly onto the entrance of an optical fiber within the excitation spectral device 500.

The movable off-axis parabolic reflector 440 has two working locations. In the first location, depicted by a solid line in FIG. 3, the reflector 440 reflects and focuses light from the reflector 411. In the second location, depicted by a dashed line in FIG. 3, the reflector 440 stays out of the way of light from the reflector 421. This arrangement allows light from either lamp to be focused at the same location. Further, the fan 417 directs air across the fins 415 of a cooling extrusion for the Xenon source 410 and onto the Tungsten source 420. This arrangement allows both sources to share a single cooling system.

The arrangement of two light sources in close proximity to each other, with their optical axes offset, and preferably at an angle of approximately 90 degrees to each other, allows for a very compact illumination system with a shared cooling system. The use of parabolic reflectors around the light sources, in combination with off-axis parabolic reflectors, results in very highly efficient coupling of light from the arc and filament into the system. Here the final focusing point of both light sources is the same. This system allows a more compact arrangement than a system which utilizes separate light source compartments with separate exit light points for each compartment, thus requiring a mechanical movement of the optical relay system to switch between sources.

Figure 4:
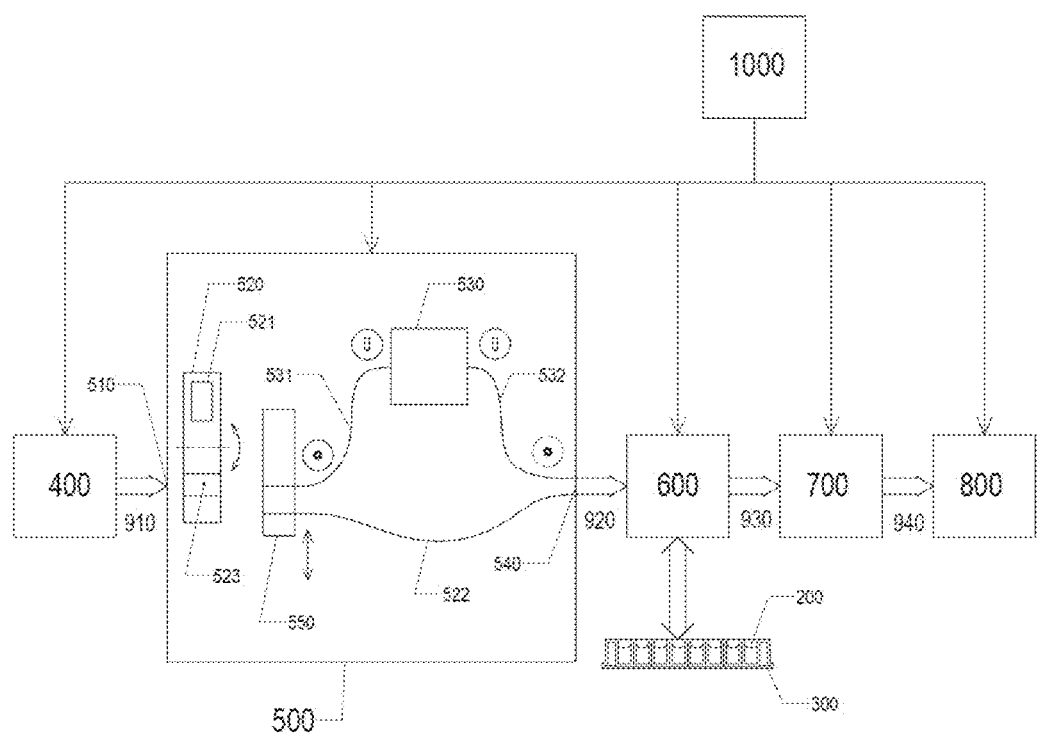
FIG. 4 illustrates an excitation spectral device according to an exemplary embodiment of the present invention.

FIG. 4 illustrates the structure of the excitation spectral device 500 according to an exemplary embodiment of the present invention. The exit portal 430 of the light source 400 is in close proximity to the input portal 510 of the excitation spectral device 500. The relay device 910 is unfilled space inside the UMS 100.

In a preferred embodiment, the excitation spectral device 500 has two spectral selection devices, which differ by the physical technology by which they separate light with different wavelengths. The first device is a filter selection device 520, which has a variety of user-replaceable filters 521. The second device is a double monochromator 530.

As shown in FIG. 4, the light exiting the light source 400 via the exit port 430 is directed to the entry point 510 of the excitation spectral device 500. Light entering the excitation spectral device 500 is then directed to the exit port 540 of the excitation spectral device 500 along one of two paths.

The first path directs the light through one of the filters 521 in the filter selection device 520, which transmits a narrow band of the light. The light then propagates through optical fiber 522 to the exit port 540. The second path bypasses the filters 521 by directing the light through hole 523 in the filter selection device 520. The light then continues via optical fiber 531, which accepts a circular image of the arc or filament spot from the light source 400 formed at the entry port 510, and shapes the light spot into a slit shape to match it to the input slit of the double monochromator 530. The monochromator 530 selects a narrow band of the light, and then the optical fiber 532 changes the shape of the light from the exit slit shape of the monochromator 530 into a circular shape that resembles the shape of a microwell 200.

The light path selector 550 can move relative to the filter selection device 520, providing the ability to guide light to the exit port 540 that was spectrally selected by the filters 521 or the monochromator 530. FIG. 5 shows the optical connections between the light source 400, the excitation spectral device 500, and the excitation-emission separation device 600 in greater detail.

Figure 6:
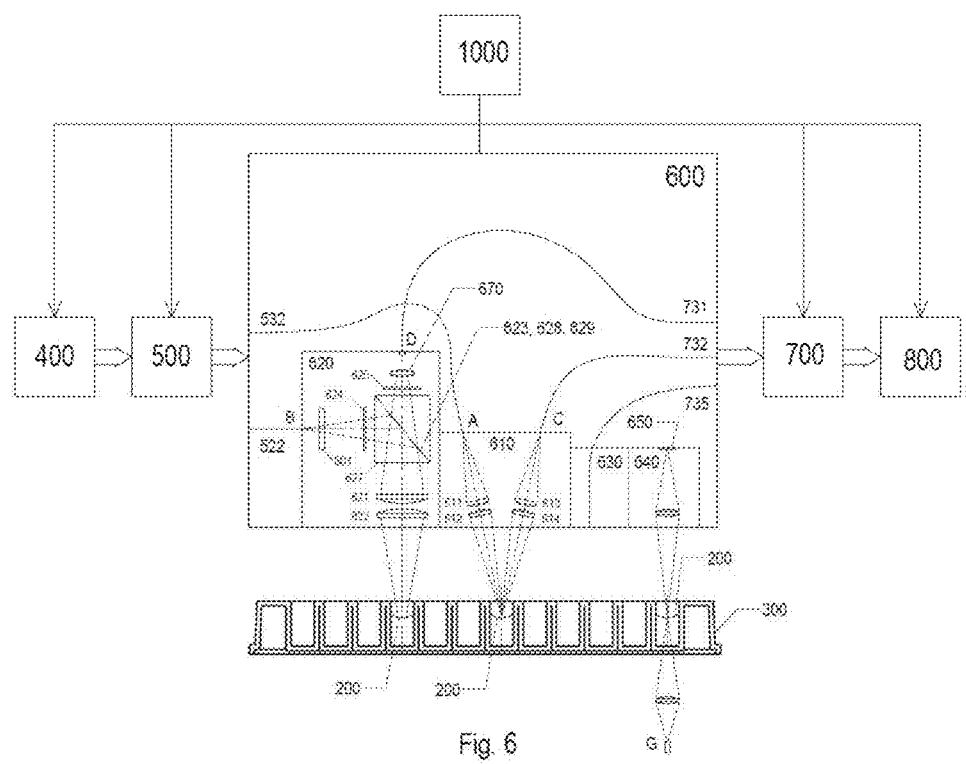
FIG. 6 illustrates an excitation-emission separation device according to an exemplary embodiment of the present invention.

FIG. 6 illustrates the structure of the excitation-emission separation device 600 according to an exemplary embodiment of the present invention. The general purpose of the excitation-emission separation device 600 is to irradiate the sample with excitation light and/or gather emission light from the sample. The excitation-emission separation device 600 can be positioned above the microwell 200 as shown in FIG. 6, or below the microwell 200. Also, the Universal Multi-detection System 100 can include two excitation-emission separation devices 600, one of which is positioned above the microwell 200, and the other of which is positioned below the microwell 200. This arrangement enables measurements of the same microwell 200 with a filter-based system and a monochromator-based system from both the top and the bottom.

In a preferred embodiment, several light paths may be used, based on the measurement technique. For absorbance measurements, the excitation and emission light are preferably collinear. As shown in FIG. 6, the absorbance measurements are conducted in block 640, in which the microwell 200 is illuminated with excitation light from below at point G. This excitation light may come from the monochromator 530 or the filter selection device 520, as shown in FIG. 5. A detector 650 is placed on the opposite side of the microwell 200 to capture emission light that passes through the sample.

For luminescence measurements, no excitation light is required, and only emission light is gathered from the sample by the excitation-emission separation device 600. In block 630, a single fiber optic bundle 735 is used to maximize the light gathering capability of the system and thus improve the signal.

For fluorescence measurements, two optical paths are available to irradiate the sample with excitation light and to gather emission light from the sample. These paths can be optimized to further enhance the overall system performance.

Block 620 depicts a first optical path for fluorescence measurements, which can use a partially reflective mirror or a dichroic mirror so that excitation light and emission light are collinear when entering and exiting the sample, respectively. Light is delivered to Block 620 by the optical fiber 522. The movable aperture 601 has several openings with diameters preferably ranging from approximately 1.5 mm to 4 mm, and is placed in front of the guide fiber 522. An image of the opening placed in front of the optical fiber 522 is formed in the microwell 200 by lenses 621 and 622. The size of the opening of the movable aperture 601 is selected to fill the microwell 200 as completely as possible with light, while preventing light from entering adjacent microwells and causing cross-talk.

The light is reflected by a partially transmitting mirror 623 on a movable holder 627. More than one mirror can be placed onto the holder 627. Some mirrors can be dichroic mirrors to improve the signal, as all excitation light is reflected towards the microwell 200, and all emission light is transmitted towards exit fiber. The dichroic mirrors can also improve the signal-to-noise ratio of the measurement system, as residual excitation light that reaches the microwell 200 and is reflected by the meniscus lens is blocked from reaching the exit fiber. The emission light from the microwell 200 is gathered onto the fiber optic bundle 731 by lenses 621, 622, and 670. A collective lens 670 in front of the fiber optic bundle 731 assures that emission light from the full depth of the microwell 200 is collected, thus maximizing the system signal.

The high energy collection characteristics of the system assure low detection limits and allow for various levels of fluid to produce acceptable results without the need to refocus the optical system based on the fluid volume. This is in contrast with, for example, the confocal style measurements described in U.S. Pat. No. 6,097,025, which uses a confocal optical system that collects light only from the small portion of the microwell.

In a preferred embodiment, linear polarizers 624 and 625 are added to the holder 627, and the same motion that positions appropriate mirrors in the light path also can be used to select polarizers for fluorescence polarization measurements. This eliminates the need for a separate mechanism to switch the polarizers, and thus improves the reliability of the system.

Block 610 depicts a second optical path for fluorescence measurements, which uses a tilted V arrangement of optics for direct well illumination and light gathering. This allows the system to channel the full amount of light from the fiber optic 532 into the microwell 200. The numerical aperture of the optics 611 and 612 is matched to the fiber optic 532 for this purpose. The cone of excitation light enters the microwell 200 and excites the contents of the microwell 200 via the first leg of the V. The emission light is collected by the second leg of the V. The numerical aperture of lenses 614 and 613 matches the exit fiber optic 732. The V is tilted with respect to the vertical plane to direct excitation light that is specularly reflected from the surface of the microwell 200 away from the light collecting leg of the V. Therefore, this arrangement introduces a spatial separation of emission and excitation light in addition to the spectral separation, and significantly improves the signal-to-noise ratio. This tilted V arrangement can also be used to conduct fluorescence polarization measurements.

The entry ports A and B of the excitation-emission separation device 600 accept fiber bundles from the excitation spectral device 500. Fibers can be positioned to direct light that is spectrally separated by filters in the excitation spectral device 500 into input B of Block 620. Fibers can also be positioned to direct light spectrally separated by monochromators in the excitation spectral device 500 into input A of Block 610. Alternatively the inputs can be reconfigured by switching fibers 522 and 532. This switching may be accomplished manually. The emission light is gathered by fibers 731 and 732 from ports C and D. The placement of fibers 731 and 732 in the exit ports C and D determines the origin of the emission light in the fibers.

Figure 7:
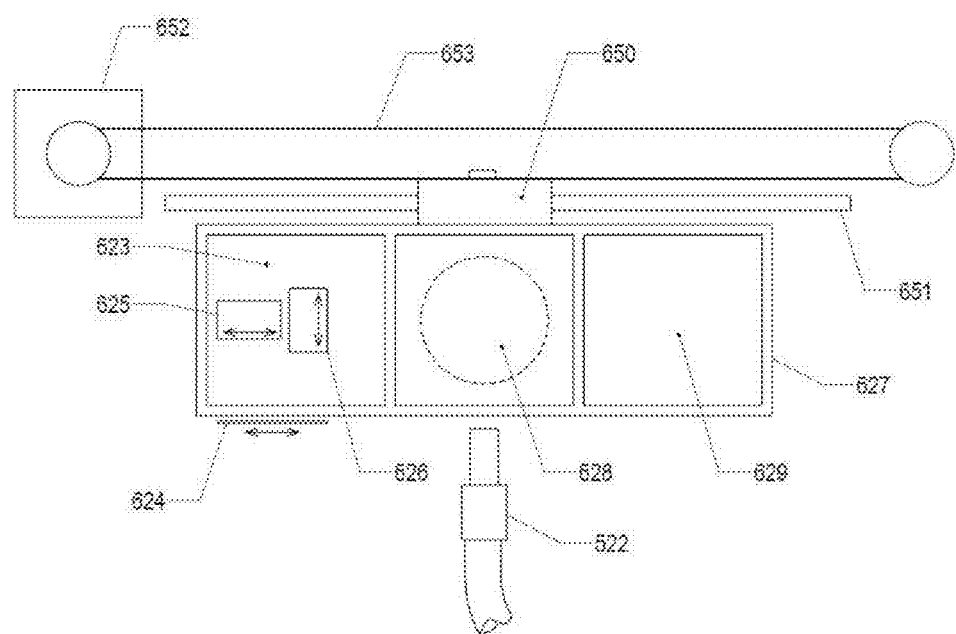
FIG. 7 illustrates a holder according to an exemplary embodiment of the present invention.

FIG. 7 illustrates the holder 627 with associated dichroic mirrors 623, 628, and 629 and linear polarizers 624, 625, and 626 according to an exemplary embodiment of the present invention. The holder 627 is affixed to the slider 650, which slides along rail 651 due to the applied force from the motor 652 through the belt 653. The holder 627 moves in a direction perpendicular to the plane defined by the optical axes of the excitation and emission light. Although two different fibers 522 and 532 could occupy the fiber position depicted in FIG. 7, for the sake of clarity only fiber 522 is shown.

In the depicted design there are five possible positions for the holder 627 relative to the fiber 522, which delivers the excitation light. The first position, which is depicted in FIG. 7, represents a situation where the center of mirror 628 is aligned with the optical axis of the fiber 522. In this position fluorescence polarization based assays cannot be conducted. If the holder 627 is moved to the left for a distance equal to the distance between the centers of mirror 628 and 629, the holder 627 will be in the second position. In the second position, the mirror 629 plays an active role, and fluorescence polarization based assays cannot be conducted.

The three other positions of the holder 627 correspond to three different situations. First, when the right third of the mirror 623 is positioned in front of the fiber 522, fluorescence polarization based assays cannot be conducted. Second, when the middle third of the mirror 623 is positioned in front of the fiber 522, the linear polarizer 624 is in the optical path of the excitation light, and the linear polarizer 626 is in the optical path of the emission light. In this case the polarization vectors of the excitation and emission light are crossed. Third, when the left third of the mirror 623 is positioned in front of the fiber 522, the linear polarizer 624 is still in the optical path of excitation light, and another linear polarizer 625 is in the optical path of the emission light. In this case the polarization vectors of the excitation and emission light are parallel. Thus the linear motion of the holder 627 not only selects which mirror is placed in the optical path, but also allows for fluorescence polarization measurements.

As shown in FIG. 7, the linear polarizers 625 and 626 have parallel surface orientations and perpendicular polarization axis orientations. They have active areas of equal sizes, and each size is comparable to the size of the cross-section of the emission light. The polarization axis of the linear polarizer 624 is parallel to the polarization axis of the linear polarizer 625, and perpendicular to the polarization axis of the linear polarizer 626. The area of the linear polarizer 624 is at least twice the area of the linear polarizer 625. The area of the mirror 623 is at least three time the area of the linear polarizer 625. The mirror 623 is partially reflective and partially transparent.

Figure 8:
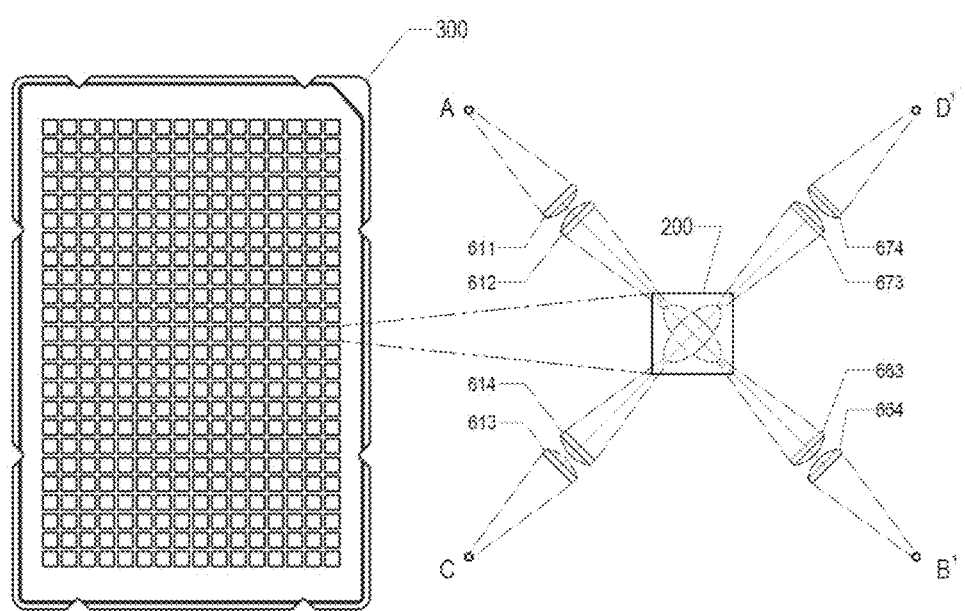
FIG. 8 shows a view of the excitation-emission separation device along vertical axes toward the microplate according to an exemplary embodiment of the present invention.

FIG. 8 shows a view from above the microplate 300, along vertical axes toward the microplate 300 of the block 610 of the excitation-emission separation device 600. Points A and B' are input portals of the excitation-emission separation device 600. Lenses 611, 612, 663, and 664 focus excitation light onto the microwell 200 in the microplate 300. Lenses 613, 614, 673, and 674 collect emission light and focus it into points C and D', which are exit portals of the excitation-emission separation device 600. Standard 384 well microplates have an upper edge with a nearly square shape. The optical axes of lenses 611, 612, 663, 664, 613, 614, 673, and 674 are oriented along the diagonals of microwells 200. Using this arrangement a reading may be taken on the same microwell 200 simultaneously via filter-based or monochromator-based spectral systems. Because the excitation light from point A is reflected toward point B' and vice versa, very little excitation light is reflected toward exit portals C and D'. Therefore, the emission light is spatially separated from the excitation light.

Figure 9:
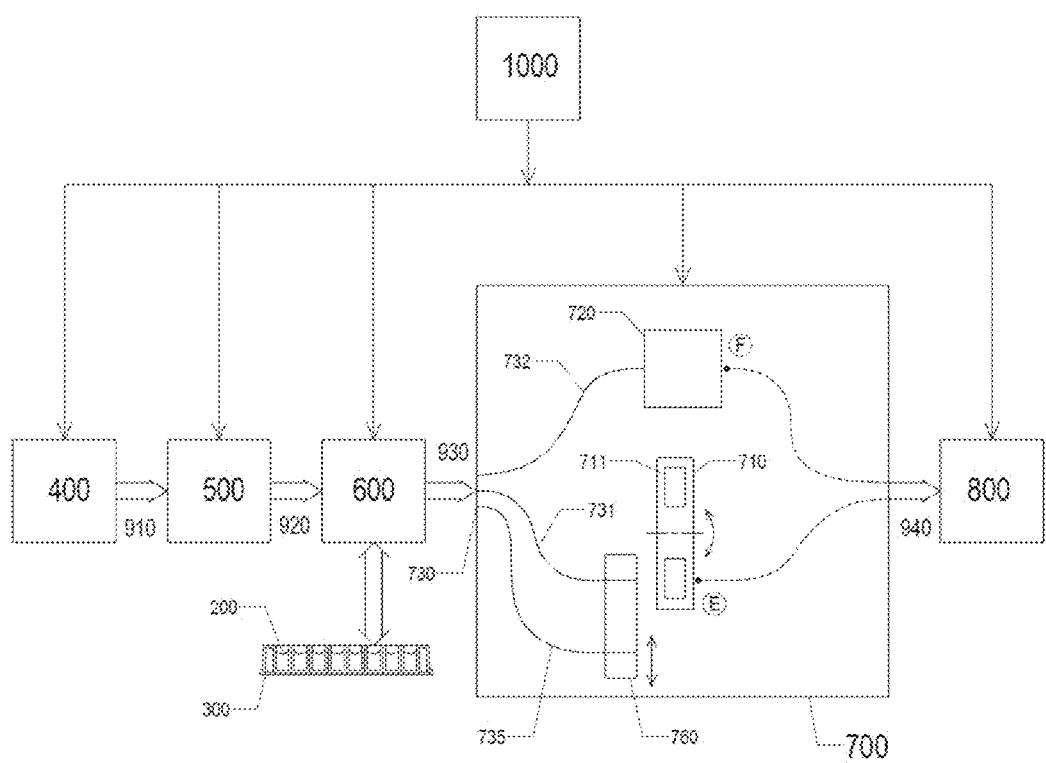
FIG. 9 illustrates an emission spectral device according to an exemplary embodiment of the present invention.

FIG. 9 illustrates the structure of the emission spectral device 700 according to an exemplary embodiment of the present invention. In a preferred embodiment, the emission spectral device 700 has two spectral selection devices, which differ by the physical technology by which they separate light with different wavelengths. The first device is a filter selection device 710, which has a variety of filters 711. The second device is a double monochromator 720. As shown in FIGS. 6 and 9, fibers 731, 732, and 735 extend from their respective locations within the excitation-emission separation device 600 into the emission spectral device 700. The selector switch 760 is used to direct light from fibers to the filter selection device 710. FIG. 9 shows that the fiber 731 from fluorescent measurement block 620 and the fiber 735 from the luminescence measurement block 630 are connected to the selector switch 760. FIG. 9 also shows that the fiber 732 from the fluorescent measurement block 610 is connected to the monochromator 720. However, the arrangement in FIG. 9 is merely exemplary, and a user can change the connections by physically switching the fiber connections within the excitation-emission separation device 600, or within the emission spectral device 700.

In a preferred embodiment, the exit portals of the excitation-emission separation device 600 are in close proximity to the input portal 730 of the emission spectral device 700. Points E and F may represent the exit portals of the emission spectral device 700. The detector 800 may comprise two photomultiplier tubes (PMTs) positioned at points E and F (not shown).

Figure 10:
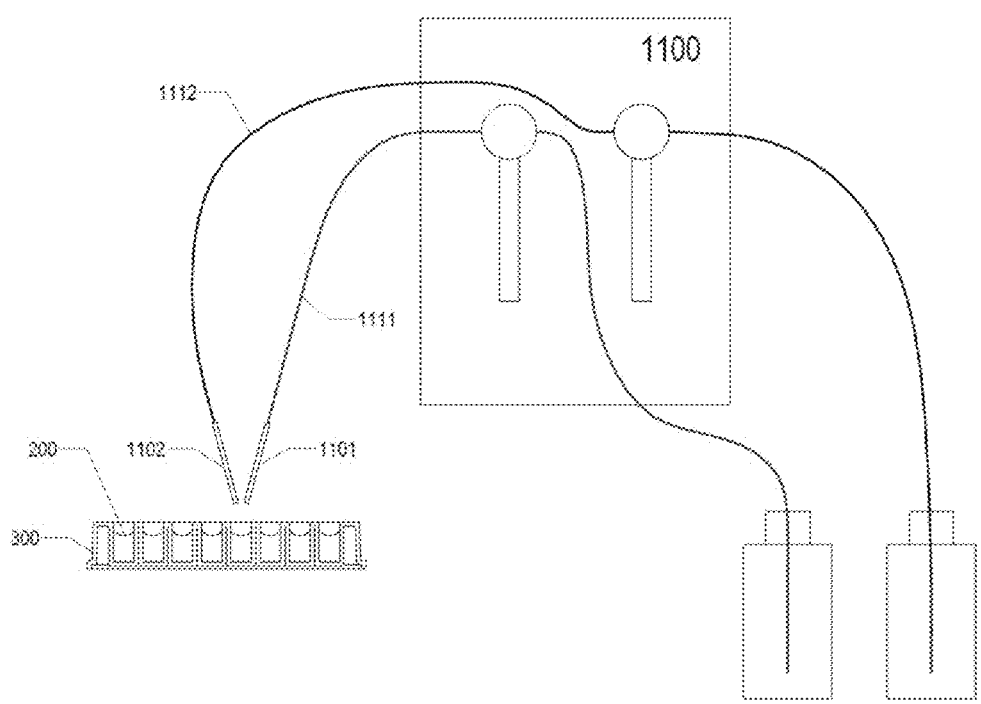
FIG. 10 shows a fluid dispenser according to an exemplary embodiment of the present invention.

FIG. 10 shows a fluid dispenser 1100 according to an exemplary embodiment of the present invention. The purpose of the fluid dispenser 1100 is to inject fluid into microwells 200 to initiate the reaction under investigation. Often the time from initiation to the time measurements have to take place is very short. Therefore, the injection ports 1101 and 1102 may be placed in close proximity to the optical reading system. Further, two separate fluid lines 1111 and 1112 may be used. Each fluid line connects to the stepper motor driven syringe drive for positive displacement fluid delivery. A three-way valve alternately connects a syringe to supply bottles on a suction stroke or to an injector line for dispensing.

In view of demand for investigating live cells, the multi-detection systems discussed below may further include the ability to image contents of the samples, along with obtaining quantitative data by fluorescence, absorbance, or luminescence, and the ability to provide in the same multi-detection analyzer a controlled gas atmosphere for samples preserving the long term viability of live cells.

Figure 11A:
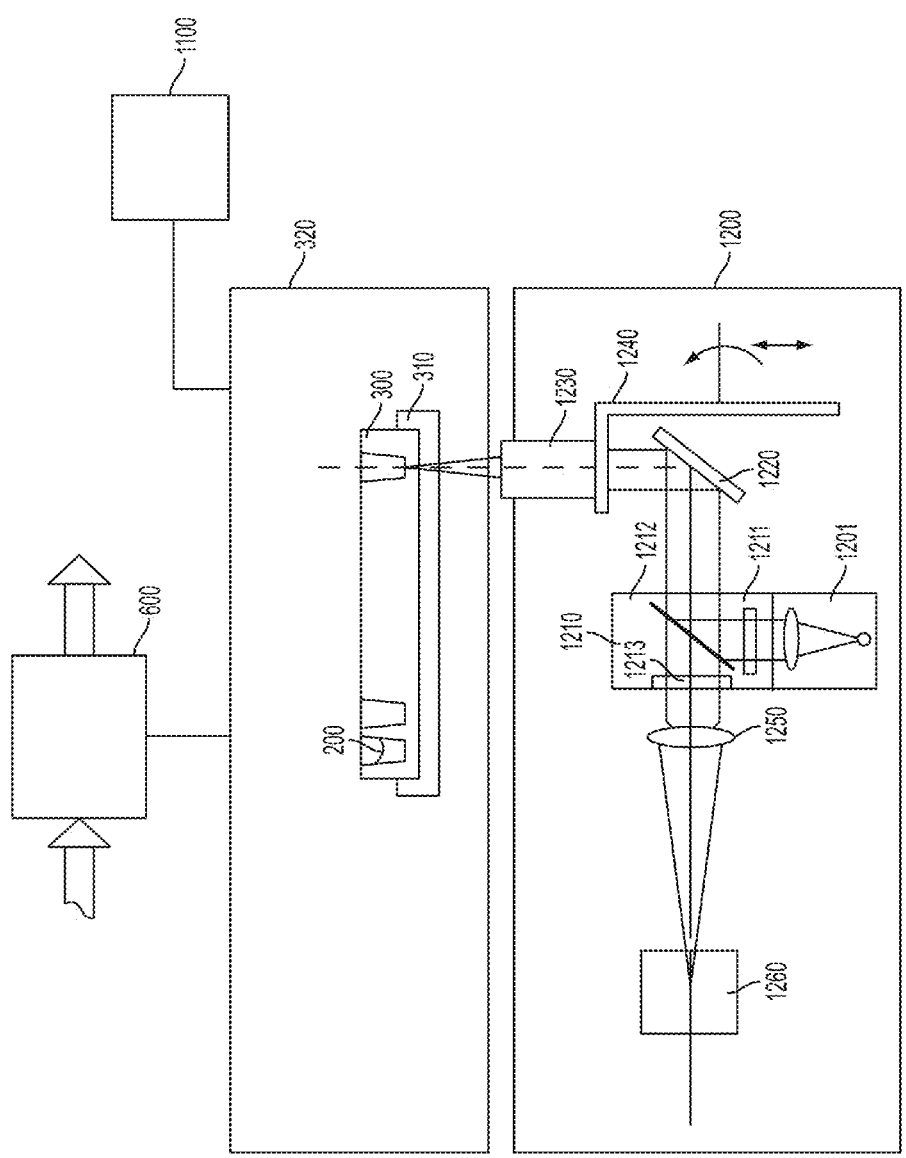
FIG. 11A illustrates a UMS according to an exemplary embodiment, in which an imaging subsystem is included in the UMS.

FIG. 11A illustrates a UMS according to an exemplary embodiment, in which an imaging subsystem is included in the UMS.

The UMS illustrated in FIG. 11A includes a measurement chamber 320, an excitation-emission separation device 600, an optional dispenser 1100, and an imaging subsystem module 1200. Samples are dispensed into the array of microwells 200 in the microplate 300. The microplate 300 is transported by the carriage 310 into the measurement chamber 320, which may be incubated, and is positioned sequentially for measurements. The microplate 300 may be a matrix-styled receptacle for holding slides or wells of sample.

The imaging subsystem module 1200 has visual access to the microwells 200 of the micro plate 300 located on the carriage 310 housed in the measurement chamber 320. Further details of the imaging subsystem module are discussed later below with respect to FIGS. 12 and 13.

The imaging subsystem module 1200 includes an independent light source 1201 such as, for example a full spectrum or single color light-emitting diode (LED), that sends light via an epi-fluorescence Excitation/Emission filter cube 1210 and mirror 1220 into a microscope objective 1230.

Figure 15:
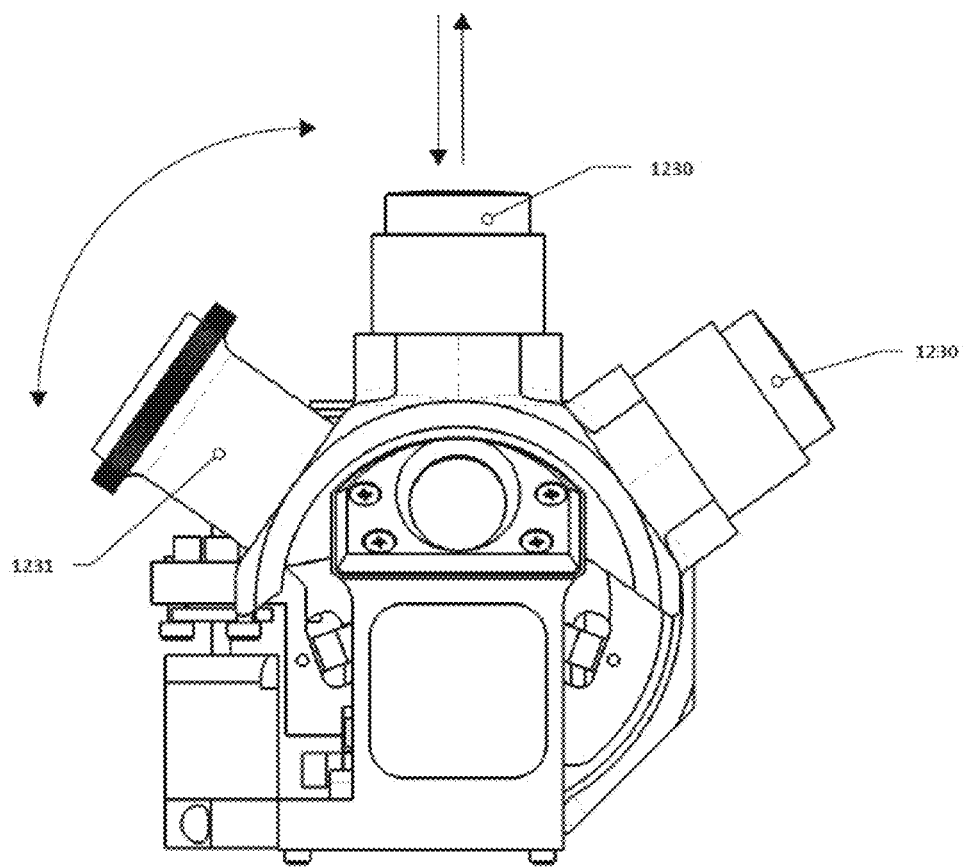
FIG. 15 illustrates a turret having objectives of the imaging module, according to an exemplary embodiment.

FIG. 15 illustrates a turret having objectives of the imaging module, according to an exemplary embodiment.

The microscope objective 1230 may be disposed on a turret 1240, which rotates and/or changes position to change objectives and moves up and down to focus the microscope objective 1230 onto the microwells 200.

By moving the turret with objectives vertically relative to microplate 300, the focusing of the objectives onto the object of interest can be accomplished. The same vertical motion allows for the entry of the objective into incubation chamber 320 and removal of the objective out of the chamber when the imaging system is not in use.

As illustrated in FIG. 15, the rotating objective turret may be mounted on motorized vertical linear way that allows insertion of one of the objectives at a time into incubation chamber and allow for focusing of the objective on the sample. A thermal barrier plug 1231 may be installed in addition to an objective 1230, and may be used to close the incubation chamber when imager is not being used for sample observations. Accordingly, maximized sample chamber temperature uniformity may be obtained when imaging modality is in use or is not being used.

The image of the microwell 200 is imaged by tube lens 1250 and a camera 1260.

Figure 14:
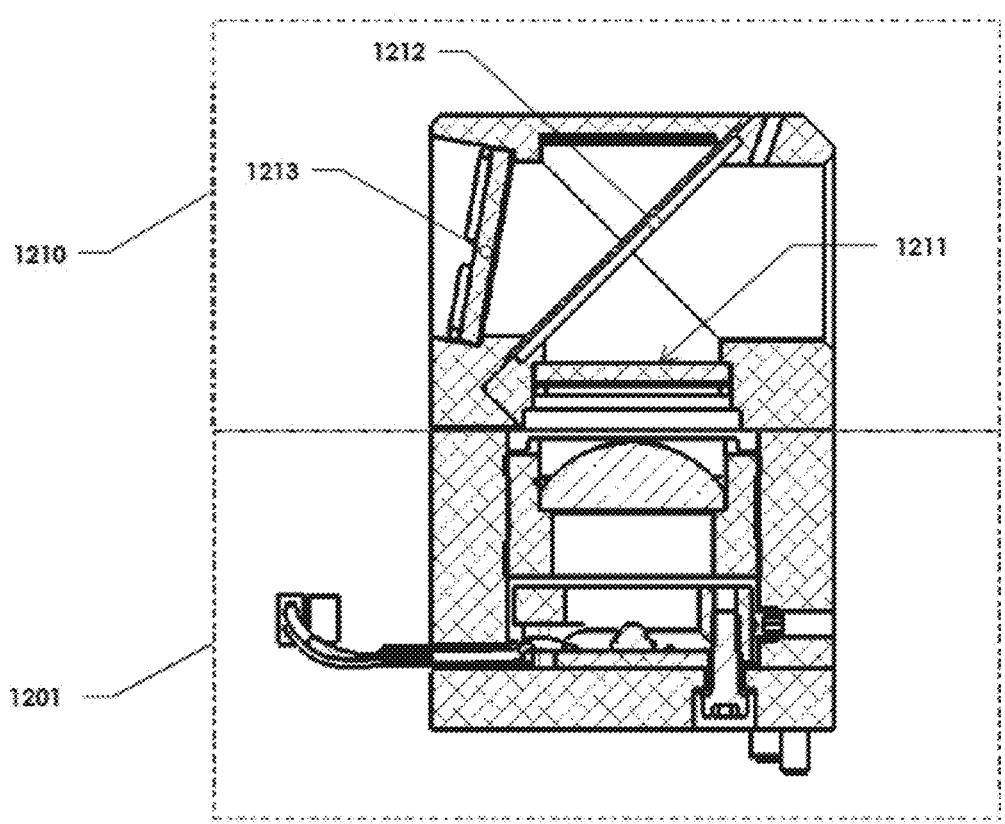
FIG. 14 illustrates an LED module of an imager, according to an exemplary embodiment.

FIG. 14 illustrates the design and positioning of the LED illumination module 1201 and the filter cube 1210. The lower LED module 1201 may include an LED and a focusing lens. The filter cube 1210 includes an excitation filter 1211, a dichroic mirror or partial mirror 1212, and an emission filter 1213.

The coordination of elements of the imaging subsystem module 1200 and motions of the microplate are controlled by a controller, which may be separately embodied or combined with a controller 1000 of FIG. 2 that also controls operation of the other multi-detection reading modalities. The controller may be a processor (e.g., central processing unit, microprocessor) that executes instructions stored in a memory for performing the imaging. The imaging of the microwell 200 contents can thus can be interlaced as part of an assay (steps in multimode plate processing discussed above). As a result, the samples that have undergone processing may be imaged.

Implementation of the imaging subsystem module 1200 is not limited to the configuration illustrated in FIG. 11A and FIG. 13 as discussed below. For example, the UMS 100 of FIG. 2 may be modified to further include the imaging subsystem module 1200. Similarly, the imaging subsystem module 1200 may be incorporated into the various embodiments of FIGS. 2 to 10 discussed throughout the application.

Figure 11B:
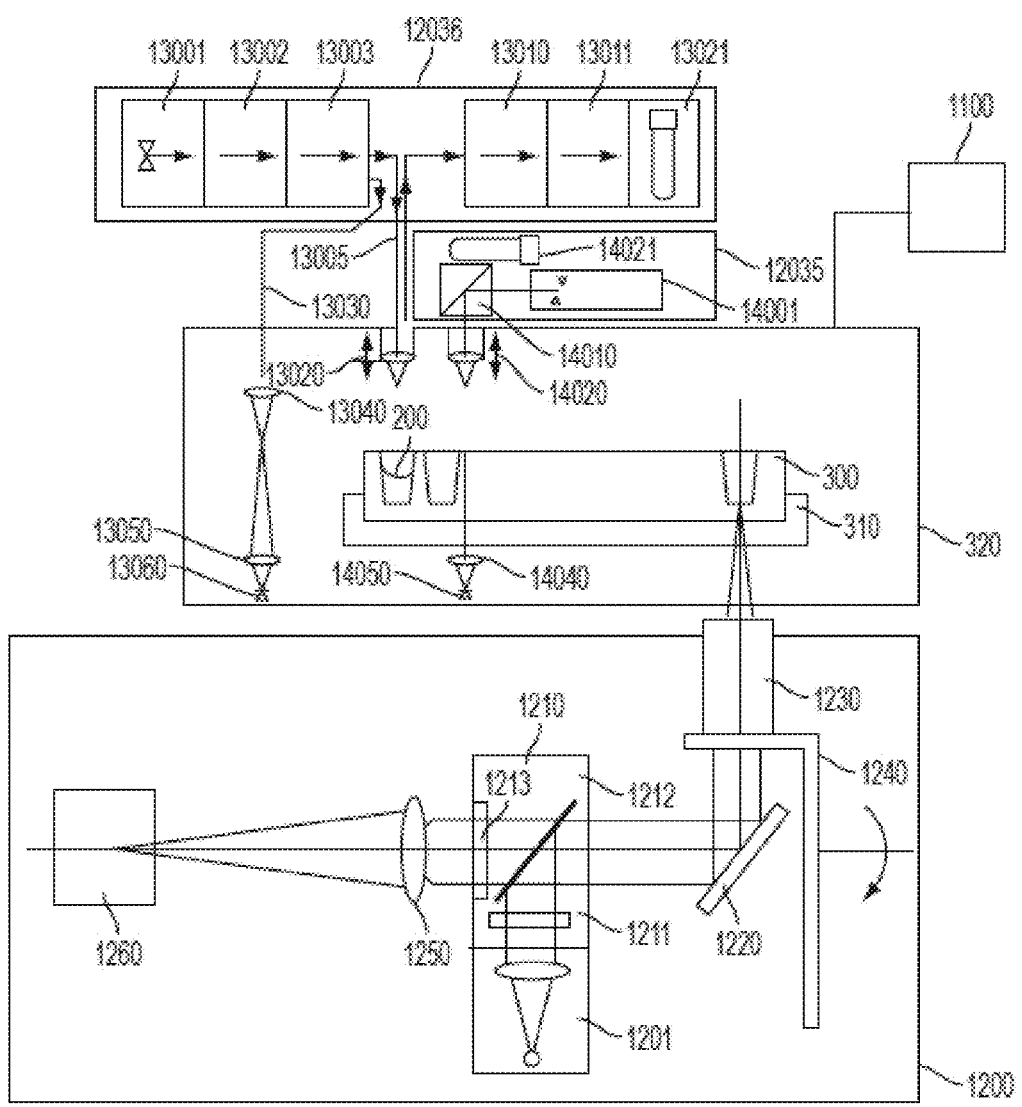
FIG. 11B illustrates a UMS according to an exemplary embodiment, in which an imaging subsystem is included in the UMS.

FIG. 11B illustrates a UMS according to an exemplary embodiment, in which an imaging subsystem is included in the UMS.

Figure 19:
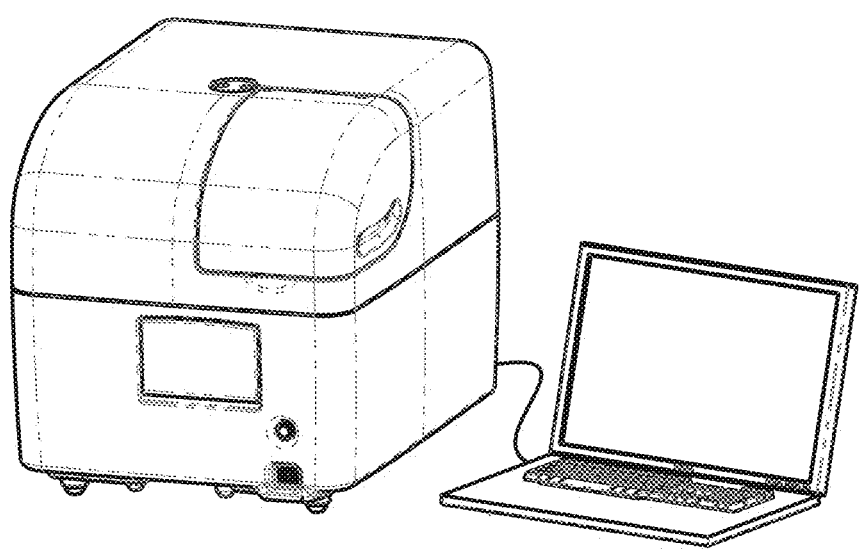
FIG. 19 illustrates a control apparatus for controlling a UMS, according to an exemplary embodiment.

The UMS illustrated in FIG. 19 includes a measurement chamber 320, a monochromator based measuring system 12036 and filter based measuring system 12035, an optional dispenser 1100, and an imaging subsystem module 1200.

As illustrated in FIG. 11B, the measurement chamber 320, the monochromator based measuring system 12036, the filter based measuring system 12035, the optional dispenser 1100, and the imaging subsystem module 1200 are separate systems that can be independently controlled and manipulated.

Though the systems of FIG. 11B may be independently controlled, the systems may be implemented in a common housing, as will be discussed below. Further, the systems may be controlled independently through a common interface, as will also be discussed below.

Samples are dispensed into the array of microwells 200 in the microplate 300. The microplate 300 is transported by the carriage 310 into the measurement chamber 320, which may be incubated, and is positioned sequentially for measurements. The microplate 300 may be a matrix-styled receptacle for holding slides or wells of sample.

Monochromator based measuring system 12036 could be used for fluorescence measurements, chemiluminescence measurements and absorbance measurements. The monochromator based measuring system 12036 may include a broad band light source 13001, double excitation monochromator 13002 (stage 1) and 13003 (stage 2). The excitation light is delivered to sample via fiber optics 13005 and focusing lens 13020. The emission light is picked up by focusing lens 13020 and via fiber bundle 13005 is guided to the double emission monochromator 13010 (stage 1) and 1311 (stage 2), and then to detector 13021. The emission path may also be used for chemiluminescence measurements. The excitation double monochromator may direct light via fiber 13030 to the absorbance measuring lenses 13040 and 13050 and onto detector 13060. The well 200 is positioned under the light beam for a specific measurement.

The filter based measuring system 12035 may be used for fluorescence measurements, chemiluminescence measurements and absorbance measurements. The filter based measuring system 12035 may include light source 14001, excitation/emission cube 14010, focusing lens 14020, and detector 14021. In case of absorbance measurements a lens 14040 focuses radiation that passed through the microwell 200 onto detector 14050.

The imaging subsystem module 1200 has visual access to the microwells 200 of the micro plate 300 located on the carriage 310 housed in the measurement chamber 320. Further details of the UMS including the imaging subsystem module are now discussed below with respect to FIGS. 12 and 13.

Figure 13:
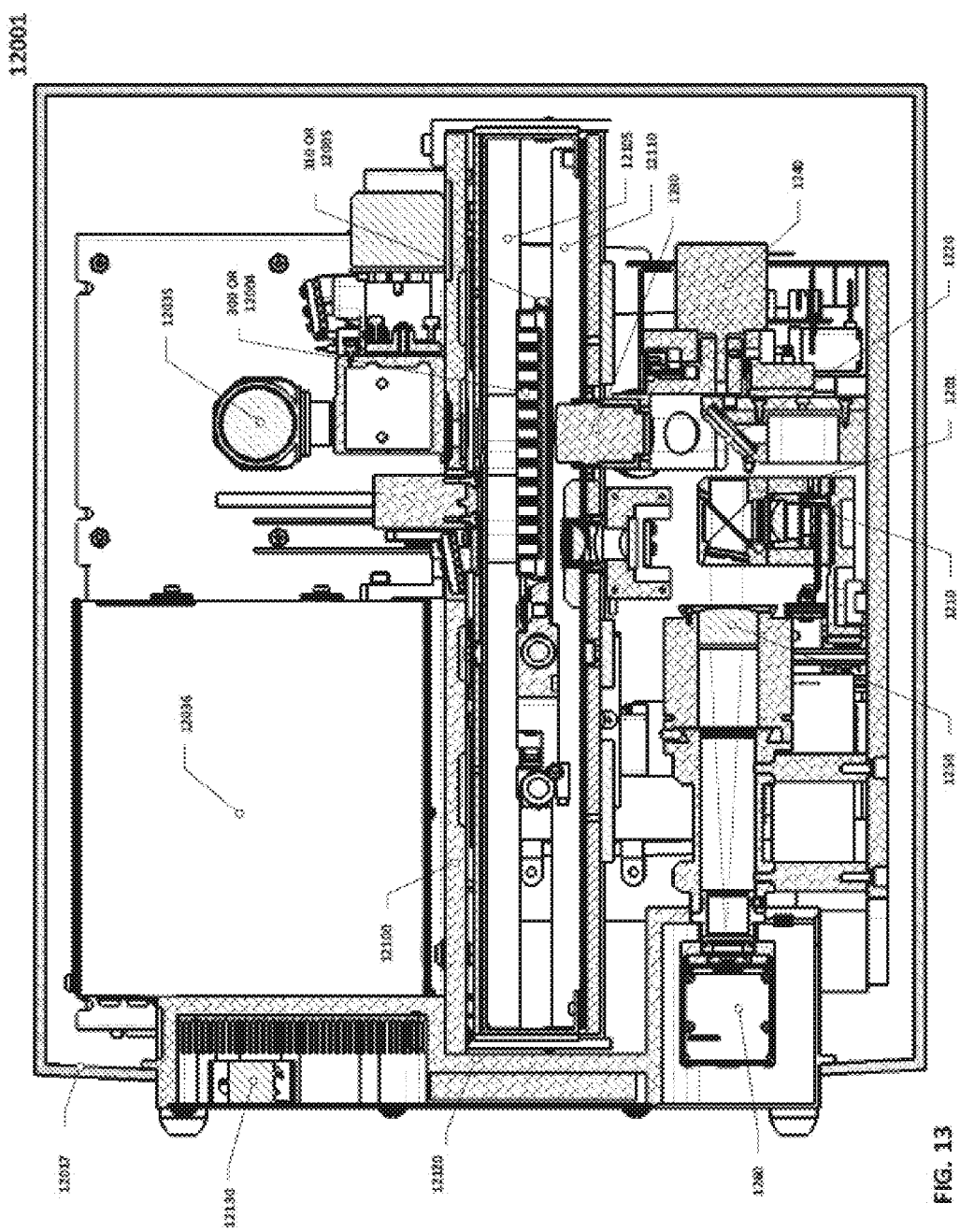

FIGS. 12 and 13 illustrate a UMS according to an exemplary embodiment, in which atmospheric control is implemented.

In view of interest on the part of researches to work with live cells and perform long kinetic studies, while obtaining both quantitative (i.e., fluorescence, absorbance, luminescence, etc.) information and qualitative information (i.e., imaging, etc.), it is important to provide an environment for sample that is conducive to the cell's long term viability. This may be accomplished by controlling gas atmosphere around the cell samples. As will be discussed below, the multi-detection analyzer of FIG. 12 allows combined quantitative modality, such as filter or monochromator based optical measurements, along with quantitative imaging of samples, and the ability to conduct experiments and obtain measurements in a controlled gas environment.

The UMS 12001 includes a single housing 12017 and a dual-purpose base structure, which includes a base 12100 and a rear plate 12120. The single housing 12017 creates one common atmosphere within the UMS. The single housing 12017 is designed to be substantially, and preferably completely, gas tight. The plate 12100 supports elements of the equipment compartments and sample compartments, but the plate 12100 does not separate the atmosphere of the elements of the equipment compartments and the sample compartments. That is to say, the elements of the equipment compartments and the sample compartments are subjected to the common atmosphere created by the housing 12017.

The sample compartment may include a micro plate 12004, similar to the microplate 300 discussed above, on carrier 12005 that is surrounded by top incubator plate 12105 and bottom incubator plate 12110, and may not be sealed by the top incubator plate 12105 and the bottom incubator plate 12110 when inside the housing 12017. The microplate 12004 may include microwells in which samples are contained.

The UMS 1201 includes a filter detection module 12035 and a monochromator detection module 12036. Both the filter detection module 12035 and the monochromator detection module 12036 may contain motors and light sources, which generate heat when operated. As testing on the samples may require an ambient temperature, the heat generated by the filter detection module 12035 and the monochromator detection module 12036 should be effectively removed from the inside of the instrument housing 12017 to maintain temperature in the sample chamber close to ambient, in particular when incubation of the sample is not required. Preferably, the generated heat may be removed without introduction of air inside the instrument and discharge of the introduced air for cooling. Particularly, as the introduction of cooling air may carry dust particulates, which may increase sample evaporation and introduce errors in sample imaging and analysis.

The heat generated by the filter detection module 12035 and the monochromator detection module 12036 in the equipment compartment is conductively channeled via base 12100 to the rear plate 12120. Heat transferred through the base 12100 to the rear plate may be removed by forced convection by a fan 12130 that is external to the housing 12017. Thus, there is no need to introduce cooling air, the flow of which and the potential contamination by which makes incubation of samples difficult, inside the housing 12017.

As a result, temperature within the housing 12017, and thus temperature of the sample compartment may be controlled.

The base of the imaging module 1200 may be attached to the same base plate that holds filter module 12035, monochromator module 12036, and microplate transmission module 310.

Figure 16:
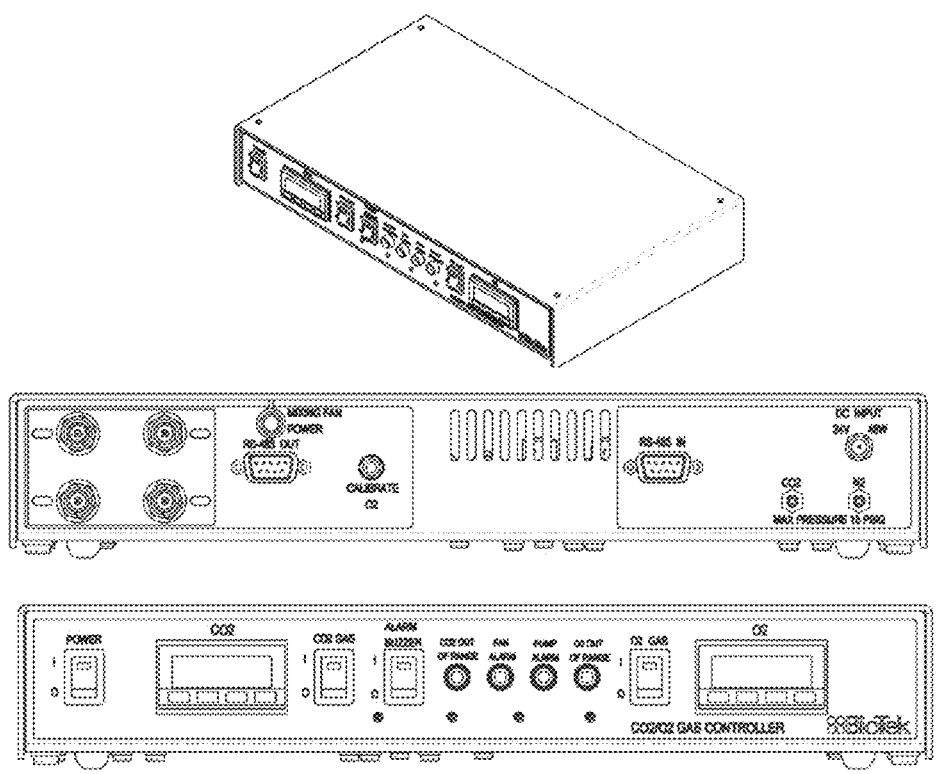
FIG. 16 illustrates views of a gas control module, according to an exemplary embodiment.

In addition to temperature control, composition of the atmosphere may also be controlled by a gas controller module, an overall view of which is illustrated in FIG. 16.

Referring to FIGS. 12 and 13, gas introduced from gas module 12006 via line 12038 and injector 12021 is dispersed via fan 12022. The lines 12038 may also include a sampling gas line coming to gas module 12006, which regulates the gas mixture delivered to the system by injector 12021. The gas module may be separately embodied or combined with a controller 1000 that may also control operation of the other multi-detection reading modalities. The introduced gas fills the single housing 12017. Accordingly, the elements of the equipment compartments and sample compartments are subjected to the introduced gas in the atmosphere within the housing 12017.

Unlike cooling air, which is conventionally drawn into the chamber to cool equipment, the introduced gas may be initially drawn into the chamber. Once the atmosphere of the housing 12017 is sufficiently stabilized, flow of the introduced gas may be terminated. Accordingly, sample incubation and measurement may then take place in a stable environment, in which both temperature and atmospheric concentration are precisely controlled.

Implementation of housing 12017, dual-purpose base structure, fans, and other elements for controlling temperature of the UMS 12001 and temperature and composition of the atmosphere within the housing 12017 is not limited to the configuration illustrated in FIGS. 12 and 13. Rather, for example, the UMS 100 of FIG. 2 may be modified to further include such temperature and atmosphere control elements. Similarly, the temperature and atmosphere control elements may be incorporated into the various embodiments of FIGS. 2 to 11 discussed throughout the application.

The housing 12017 illustrated in FIGS. 12 and 13 may be a clam shell design, consisting of two half enclosures that are mated together around the main mechanical assembly. The main mechanical assembly by be suspended in the enclosed housing 12017 when both halves of the clam shell are mated together. To ensure that the completed housing 12017 is essentially gas tight, for example, a gasketing material could be used on the interface between the two halves. The use of the gasketing material is not limiting, as other forms of sealing may be employed.

The controlled environment of FIGS. 12 and 13 enables controlled ambient conditions, such as temperature and/or atmospheric concentration (e.g., $CO_2$ and $O_2$ concentration) around the samples. When multiple measurement modalities including imaging studies are required, all dedicated instruments should to be placed into environmental chamber, which creates problems with access and a need for manual intervention during a long term experiment. However, the controlled environment of FIG. 12 permits easy long term, multifaceted experiments to be conducted.

As discussed above, exemplary embodiments of the present invention provide a Universal Multi-detection System for determining fluorescence, chemiluminescence, and/or light absorbance of a sample in a microplate that allows the user to reconfigure and optimize the measurement system for a particular modality. The Universal Multi-detection System allows the user to choose the best measurement method for his assay. The user can select interference filters for their low detection limits and ability to run FP, TRF, and HTRF measurements with state of the art results, dual monochromators for their wavelength flexibility and spectral scanning, or a combination of both filters and monochromators. Both the excitation spectral device 500 and the emission spectral device 700 may contain interchangeable filter systems and monochromators.

In addition to providing unmatched flexibility, the Universal Multi-detection System also opens an avenue to run experiments that were not previously possible. For example, in the fluorescence mode, when only a small amount of an unknown fluorofore is available and it is not possible to increase the signal in the monochromator-based system by increasing the sample concentration, the user can obtain rough excitation and emission scans by using monochromators 530 and 720 in the excitation spectral device 500 and the emission spectral device 700, respectively. Based on these initial excitation and emission scans, the user can then select an appropriate filter 521 to excite the sample with light that causes much stronger emission from the sample. The stronger emission spectrum can then be re-recorded. The user can also select a filter 711 to replace the emission monochromator 720 and re-record the excitation spectrum. It is important to have high-quality measurements of both the excitation spectrum and the emission spectrum. This process increases the emission signal and the signal-to-noise ratio, resulting in improved excitation and emission spectra, as compared with spectra obtained with just a monochromator-based system. It also allows a user to work with an unknown sample, and optimize the measurement conditions for that sample.

This approach can also be used to achieve maximum sensitivity in end-point reads. The user can select particular excitation wavelengths by using a monochromator 530 in the excitation spectral device 500, and transmit the emission light through a filter 711 in the emission spectral device 700. A similar benefit can be obtained by using a filter 521 in the excitation spectral device 500 with a monochromator 720 in the emission spectral device 700 during an end-point read. These methods are particularly suited to enhancing performance of environmentally sensitive labels, where variations in conditions give rise to perturbations of excitation or emission spectra, such as ion sensitive probes, pH sensitive probes, spectral shifts in polar dyes with conjugation, and binding and membrane probes.

Figure 17:
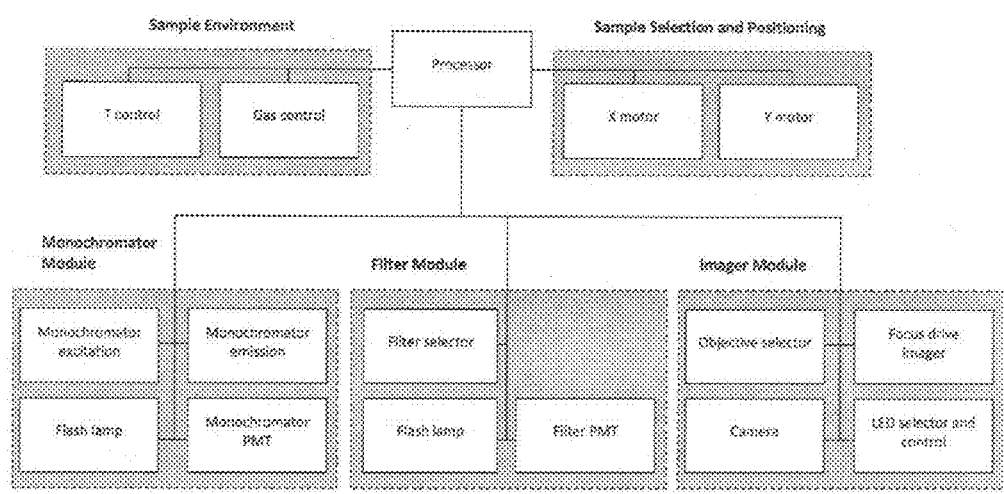
FIG. 17 is a functional block diagram that illustrates control of modalities, according to an exemplary embodiment.

FIG. 17 is a functional block diagram that illustrates the control of modalities of a UMS, according to an exemplary embodiment.

As illustrated in FIG. 17, operation of the modalities of the UMS may be controlled by a central control unit (e.g., processor, CPU, microprocessor, etc.). The processor may be connected to communicate with and control elements of the sample environment, elements of sample selection and positioning, elements of the monochromator module, elements of the filter module, and elements of the imager module.

Elements of the sample environment under control may provide temperature control and gas control, as discussed above.

Sample positioning may be controlled through the use of motors for positioning samples in any of X and Y directions.

Elements of the monochromator module under control may include monochromator excitation, monochromator emission, monochromator PMT, and a light source such as a flash lamp.

Elements of the filter module under control may include the filter selector, a filter PMT, and a light source such as a flash lamp.

Elements of the imager module under control may include an objective selector, an image capturing device such as a camera, a focus drive imager, and an LED selector and control.

Figure 18:
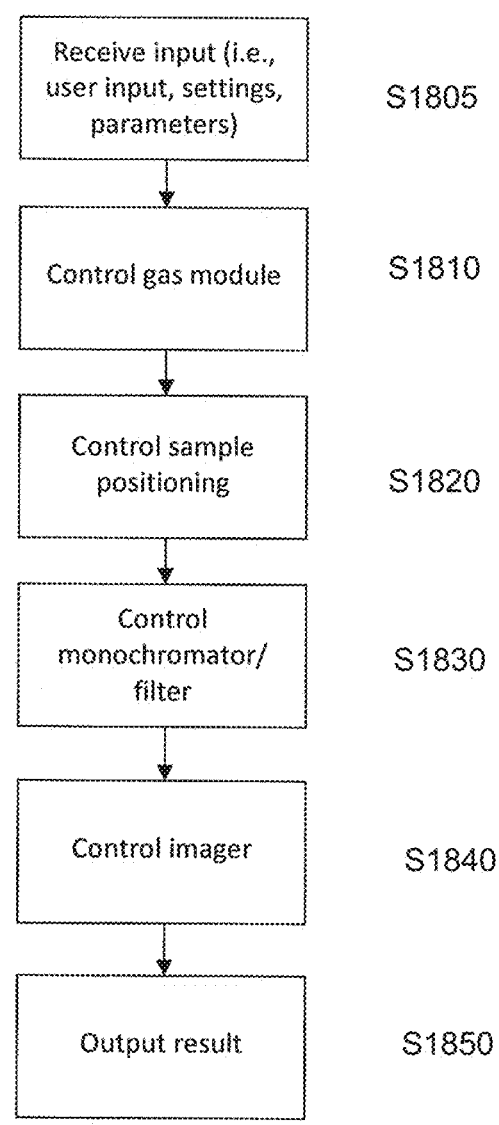
FIG. 18 is a flowchart of a control method of a UMS, according to an exemplary embodiment.

FIG. 18 is a flowchart of control method of a UMS, according to an exemplary embodiment.

Control of the UMS may be coordinated through use of the processor, as discussed above with respect to FIG. 17. Input to the UMS (step S1805) may be accomplished through a local user interface of the UMS, such as a touch pad, or through communication with the UMS over a wired or wireless connection, such as over a network.

In the case of input to the UMS, input may be performed through the use of a user interface or graphical user interface displayed on a computer or other terminal that executes a control application.

The input may be user input, such as setting and parameters for executing control of the UMS.

In response to receiving input, control of the UMS may be effectuated through the various elements of the UMS, discussed above regarding FIG. 17. For example, in response to receiving user input, the UMS may be controlled to execute a gas control procedure of the gas module (step S1810), a sample positioning control procedure to control positioning of samples (step S1820), a monochromator and/or filter control procedure to control operations of the monochromator and/or filter (step S1830), an imager control procedure to control the imager (step S1840), and to output a result of the controlling of the elements of the UMS (step S1850).

Although control is presented as illustrated in FIG. 18, elements may be individually controlled in any sequence, and control of all elements is not required. Accordingly, the multiple modalities of the UMS may be controlled in a single assay. Additional aspects of the control of the UMS will be discussed below with respect to FIGS. 19 to 29.

The control method illustrated in FIG. 18 may be implemented through execution of a processing unit (e.g., CPU) controlling elements of the UMS by executing one or more control programs. The programs may be stored in a memory (i.e., RAM, ROM, flash, etc.), or other computer-readable medium (i.e., CD-ROM, disk, etc.). The program may be executed locally by the UMS, or by a control apparatus, such as a computer that transmits commands to be executed by the UMS.

FIG. 19 illustrates a control apparatus for controlling a UMS, according to an exemplary embodiment.

As discussed above with respect to FIGS. 17 and 18, the UMS may be controlled through communication with a control apparatus. The control apparatus may be a laptop computer, as illustrated in FIG. 19. Communication between the UMS and the control apparatus may be conducted locally through a USB cable, as illustrated in FIG. 19.

The control apparatus is not limited to the laptop computer, but may be any apparatus including a processor that executes control software for providing a user interface (UI) for controlling operations of the UMS. The control software may be installed on the control apparatus, or executed by the control apparatus in communication with a server device that hosts the control software, for example over a network such as the Internet.

The control apparatus executing the control software may issue commands to the UMS over the USB connection, though communication may be performed using other wired techniques, such as Ethernet, or wireless techniques such as infrared or wireless communication. The communication may be direct, for example over the USB connection, or accomplished through a network of intermediary devices, such as routers and switches. The network may be a local network, such as a local area network (LAN), or over a public network, such as the Internet.

Figure 20:
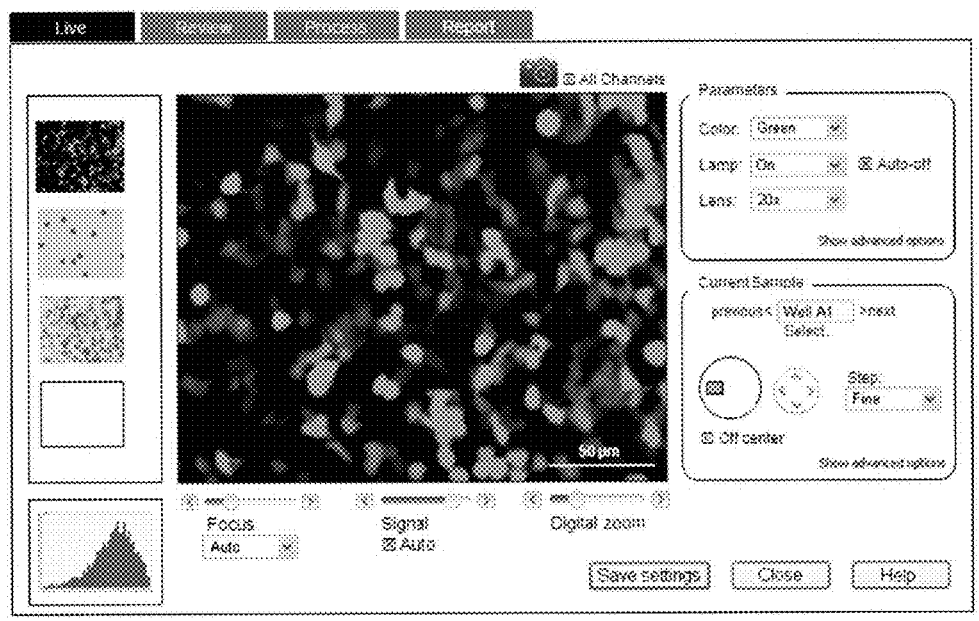
FIG. 20 illustrates operations of an imaging subsystem of a UMS, according to an exemplary embodiment.

FIG. 20 illustrates operations of an imaging subsystem of a UMS, according to an exemplary embodiment.

As discussed above, the UMS may include an imaging subsystem for imaging a sample.

The control software may include a UI for the imaging subsystem. The UI for the imaging subsystem may receive user inputs for controlling the imaging subsystem to image a sample.

As illustrated in FIG. 20, the UI for the imaging subsystem may control various aspects of the imaging subsystem including, but not limited to, parameters such as color, lamp power, and lens magnification.

The UI for the imaging subsystem may further select at least one well at a position of a microplate and a position of imaging a particular portion the well. As illustrated in FIG. 19, the imaging subsystem may control the UMS to image individual samples one at a time, but may also be controlled to image an entire microplate.

Other options of the UI for the imaging subsystem may be used to control focus, signal, and digital zoom.

The settings of the imaging subsystem may be stored in memory, and retrieved for subsequent imaging of additional samples.

The UI for the imaging subsystem may be employed to view live samples in real-time, review images of previous samples, and view reports of sample images.

As illustrated in FIG. 19, the imaging subsystem may control the UMS to image individual samples one at a time, but may also be controlled to image an entire microplate.

Figure 21:
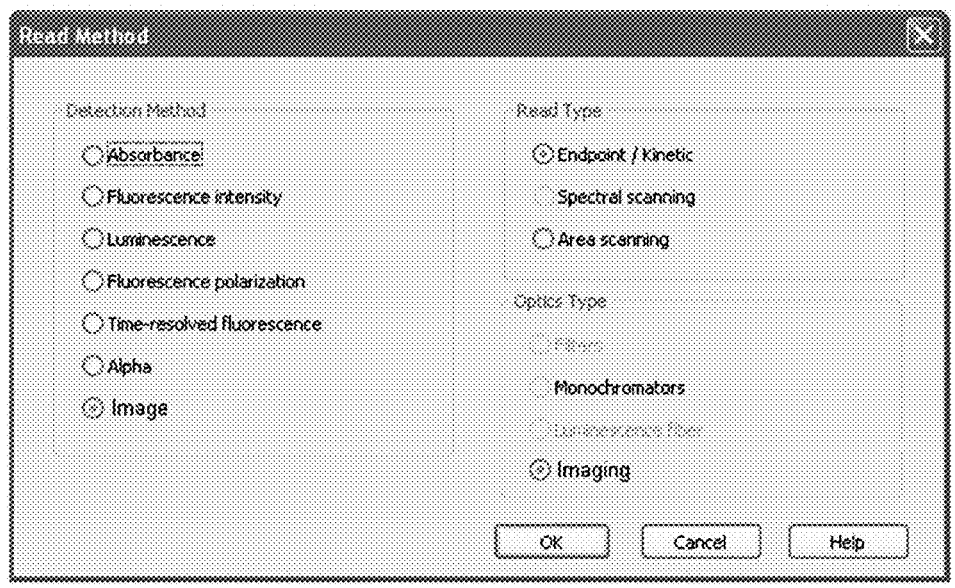
FIG. 21 illustrates mode selection of operations of a UMS, according to an exemplary embodiment.

FIG. 21 illustrates mode selection of operations of a UMS, according to an exemplary embodiment.

As discussed above, the UMS may include an analysis subsystem for analyzing a sample and an imaging subsystem for imaging the sample.

FIG. 21 illustrates the configuration in which the imaging by the imaging subsystem is selected. Naturally, other modes of the analysis subsystem, such as absorbance, luminescence, or the like, may be selected.

When selecting an analysis mode, the optics may also be selected by the user, such as monochromator or filter. Alternatively, the optics may be automatically selected based on the mode selection.

A read type may also be selected, such as endpoint/kinetic, spectral scanning, or area scanning. Again, the read type may be selected by the user or automatically selected based on the mode selection.

Figure 22:
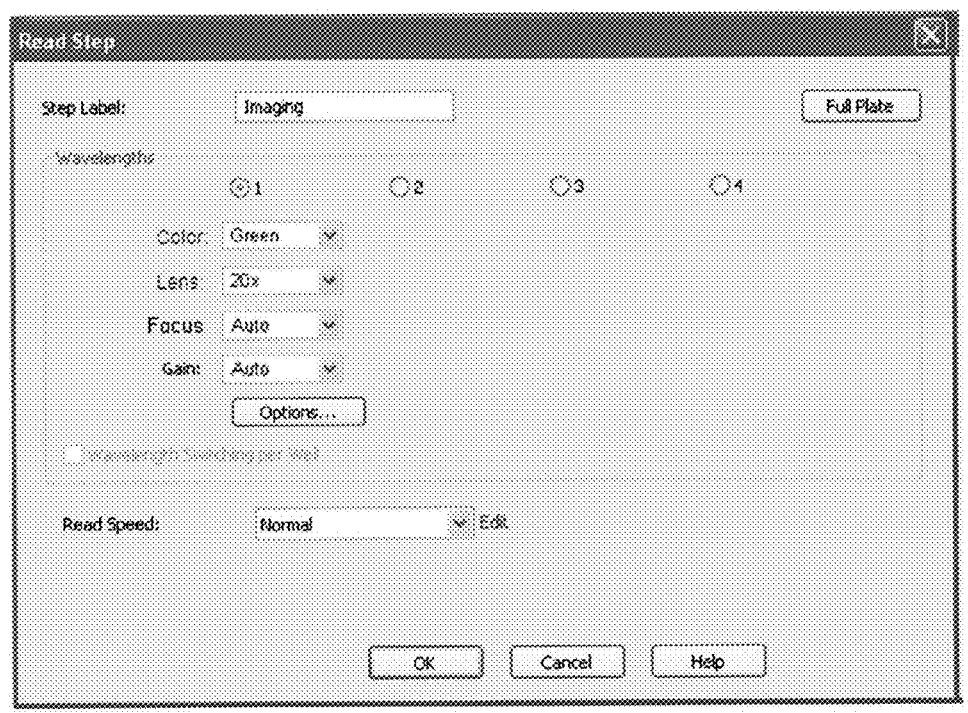
FIG. 22 illustrates parameter settings of an imaging subsystem of a UMS, according to an exemplary embodiment.

FIG. 22 illustrates parameter settings of an imaging subsystem of a UMS, according to an exemplary embodiment.

Upon selection of a detection mode, additional parameters may be set.

In the case of selecting the imaging mode illustrated in FIG. 21, the parameters for the selected imaging mode are shown in FIG. 22.

The selectable parameters may include color, lens, focus, gain, and additional options, which are associated with the selected mode. An imaging speed and color for sample imaging may also be selected per well, or for the entire microplate.

Figure 23:
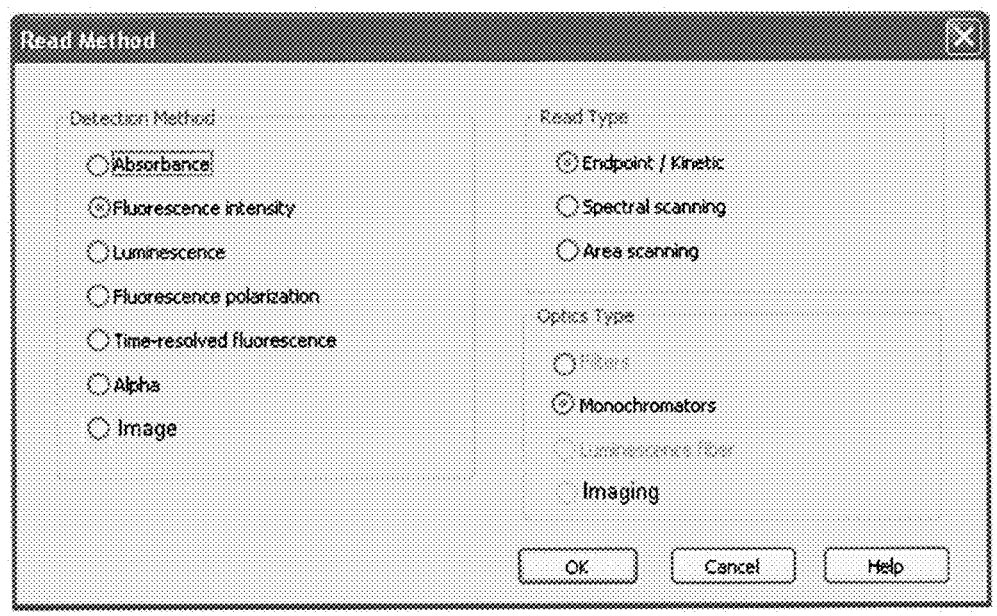
FIG. 23 illustrates parameter settings of an analysis subsystem of a UMS, according to an exemplary embodiment.

FIG. 23 illustrates parameter settings of an analysis subsystem of a UMS, according to an exemplary embodiment.

As discussed above, the UMS may include an analysis subsystem for analyzing a sample and an imaging subsystem for imaging the sample.

FIG. 23 illustrates the configuration in which the analyzing by the analysis subsystem is selected. While the detection mode selected in FIG. 23 is the fluorescence intensity analysis, other modes of the analysis subsystem, such as absorbance, luminescence, or the like, may be selected.

When selecting an analysis mode, the optics may also be selected by the user, such as monochromator or filter. Alternatively, the optics may be automatically selected based on the mode selection. In the case of the fluorescence intensity analysis, the optics for luminescence fiber and imaging may be automatically deselected (e.g., grayed out).

Figure 24:
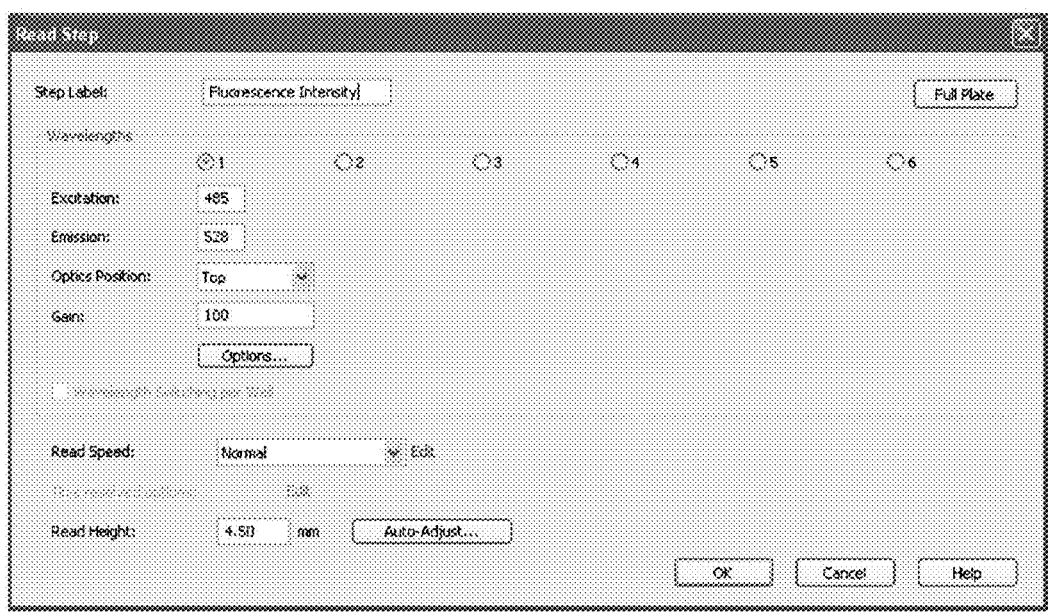
FIG. 24 illustrates parameter settings of an analysis subsystem of a UMS, according to an exemplary embodiment.

FIG. 24 illustrates parameter settings of an analysis subsystem of a UMS, according to an exemplary embodiment.

Upon selection of a detection mode, additional parameters may be set.

In the case of selecting the fluorescence analysis mode illustrated in FIG. 23, the parameters for the selected fluorescence mode are shown in FIG. 24.

The selectable parameters may include excitation, emission, optics positioning, gain, and additional options, which are associated with the selected fluorescence analysis mode. A read speed, read height, and a wavelength for sample analysis may also be selected per well, or for the entire microplate.

Figure 25:
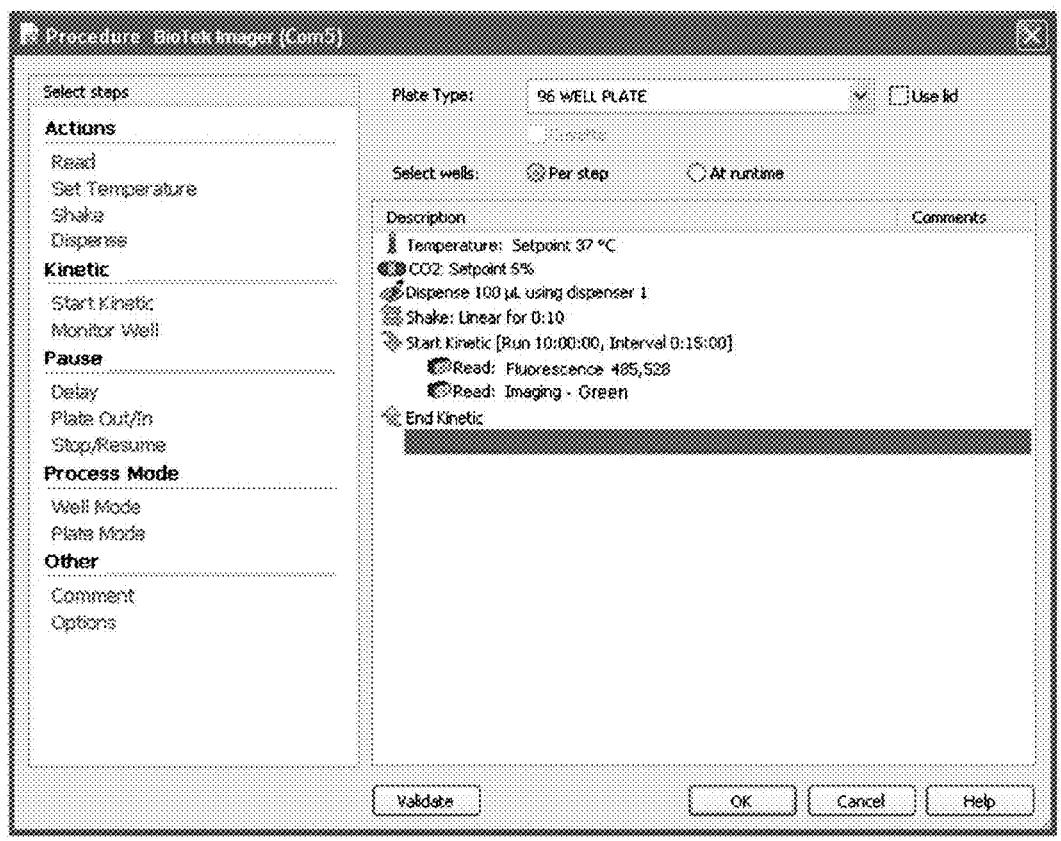
FIG. 25 illustrates settings of multiple subsystems of a UMS, according to an exemplary embodiment.

FIG. 25 illustrates settings of multiple subsystems of a UMS, according to an exemplary embodiment.

As discussed above, in addition to the imaging and analysis subsystems, the UMS may also include a temperature subsystem and a gas control subsystem.

FIG. 25 illustrates a procedure in which an assay temperature is set to 37 degrees Celsius by control of the temperature control subsystem, a carbon dioxide level is set to 5% by control of the gas control subsystem, a reagent is automatically dispensed, then shaking happens for 10 seconds, a kinetic measurement is initiated to automatically follow fluorescence and image changes over a 10 hour time period every 15 minutes, according to controls of the imaging and analysis subsystems.

Additional controls may be provided for independently controlling the various subsystems. For example, control operations of the various subsystem operations may be changed, paused, stopped, resumed, or scheduled based on a delay or timer.

Figure 26:
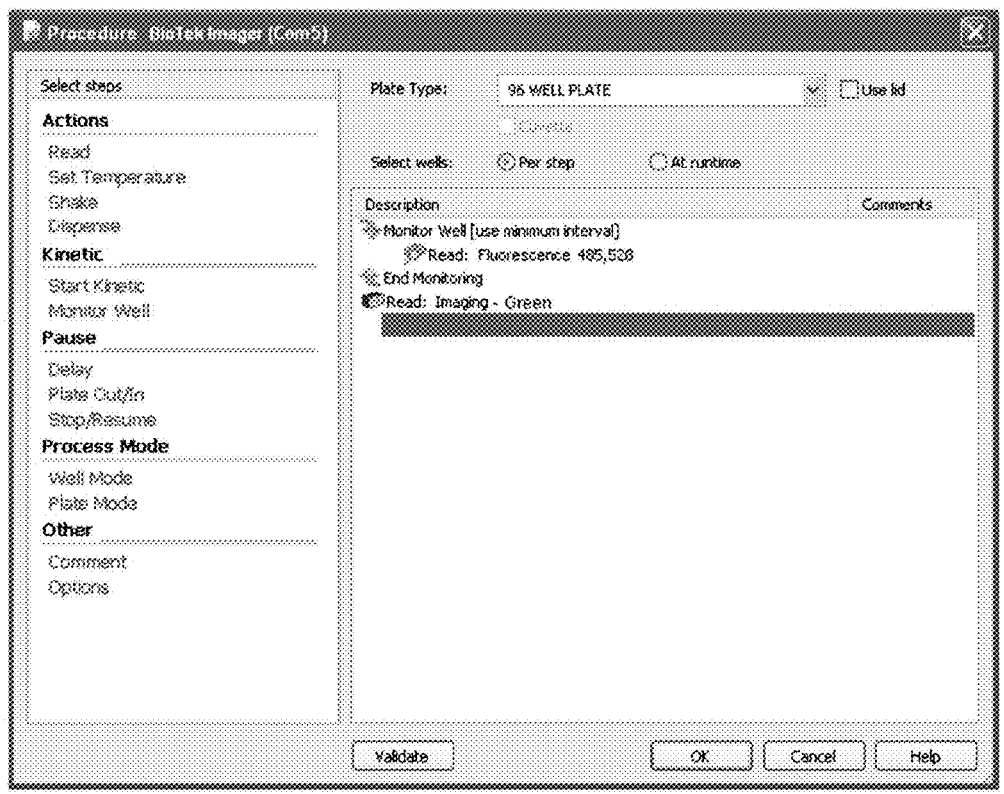
FIG. 26 illustrates monitoring operations by an analysis subsystem and conditional imaging by an imaging subsystem of a UMS, according to an exemplary embodiment.

FIG. 26 illustrates monitoring operations subsystems of a UMS, according to an exemplary embodiment.

As illustrated in FIG. 26, subsystems may be programmed by the user. In FIG. 26, fluorescence signal is monitored automatically, and when a pre-set condition is met, imaging starts. Based on the pre-set condition programmed by the user, only wells of interest matching the condition may be imaged.

The programming conditions may be stored to memory, and recalled from memory for use with additional samples. Alternately, the programming conditions may be modified as needed, and stored as additional programming conditions.

Default programming conditions may be provided in a UMS, for selection by a user according to frequently used programs. Alternately, new programming conditions may be adopted according to input of the user.

Figure 27:
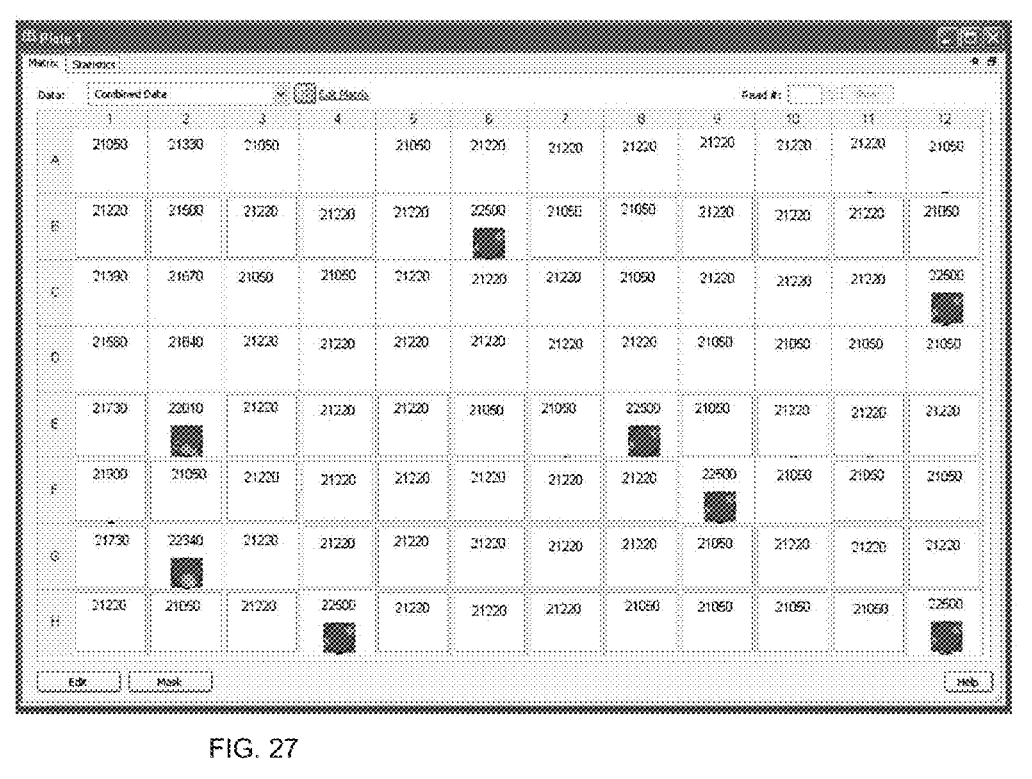

FIG. 27 illustrates results of operations of an analysis subsystem of a UMS, according to an exemplary embodiment.

As discussed above, programming conditions may be input by the user and the programming conditions may be carried out by the UMS.

FIG. 27 illustrates results obtained from executing the programming conditions illustrated in FIG. 26.

As illustrated in FIG. 27, wells have been read using standard fluorescence measurement, wells with initial result above 22,000 are automatically imaged, and a thumbnail image is displayed for these wells, in combination with the fluorescence result.

Alternately, as opposed to each well, only those wells satisfying the pre-set conditions may be displayed, thereby increasing viewing efficiency.

The use of such a programmed process allows for faster reading of sample and limiting the size of the final data file since only the relevant wells are imaged.

Figure 28:
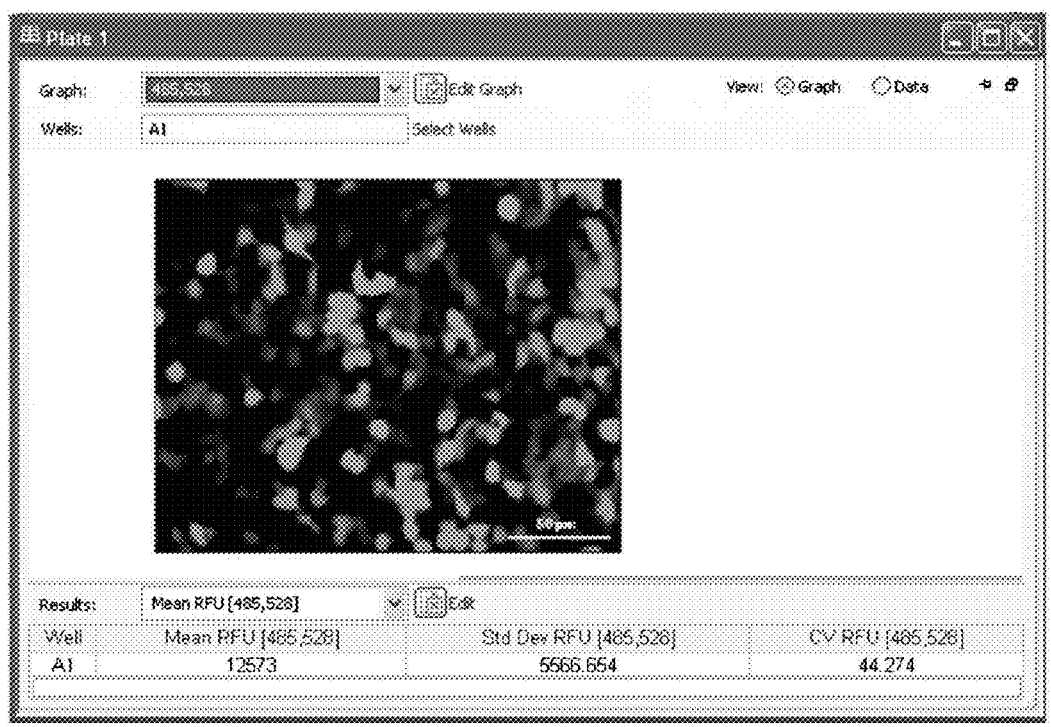
FIG. 28 illustrates a detailed result of operations of an analysis subsystem of a UMS, according to an exemplary embodiment.

FIG. 28 illustrates a detailed result of operations of an analysis subsystem of a UMS, according to an exemplary embodiment.

As discussed above, a programmed process may be executed by the UMS and results may be cumulatively displayed.

As illustrated in FIG. 28, the results may be selectively displayed. For example, a "well zoom" may be displayed when clicking on one of the image thumbnails.

In addition to the zoom image of the well, other statistics, graphs, charts, and raw data of the well may be presented.

Figure 29:
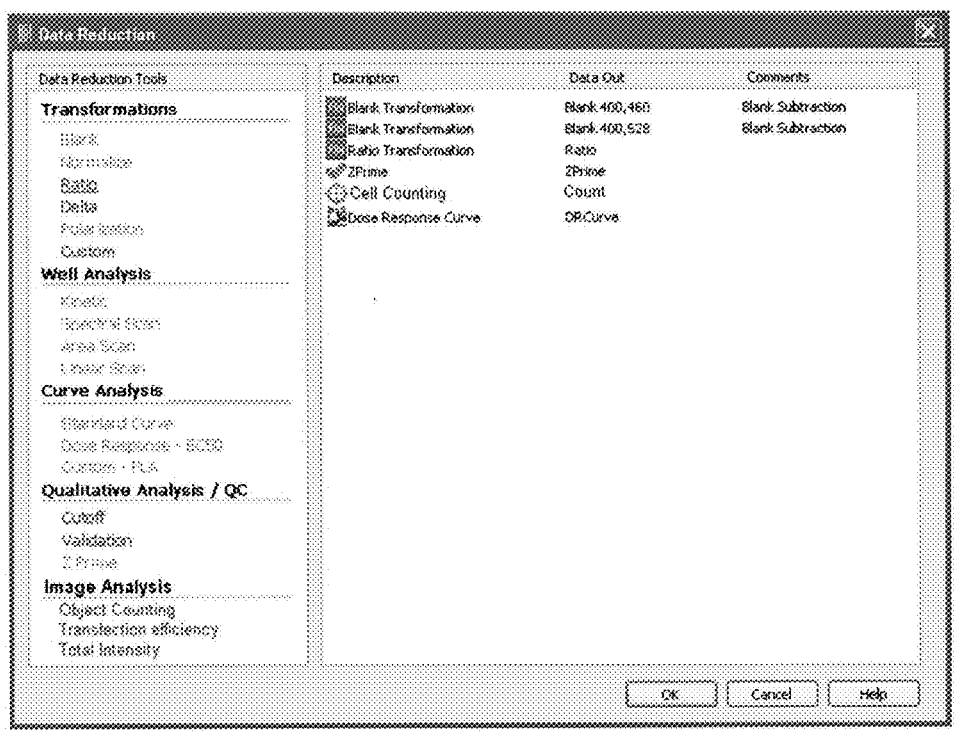
FIG. 29 illustrates data reduction options for combined analysis and imaging subsystems of a UMS, according to an exemplary embodiment.

In addition to display of results, data reduction tools may be provided, as shown in FIG. 29.

For example, "Image Analysis" tools may be provided for object counting, transfection efficiency, and total intensity. As illustrated in FIG. 29, "Cell Counting" based on image analysis may be an exemplary tool.

Exemplary embodiments of the present invention have been described for illustrative purposes, and those skilled in the art will appreciate that various modifications, additions and substitutions are possible without departing from the scope and spirit of the invention as disclosed in the accompanying claims. Therefore, the scope of the present invention should be defined by the appended claims and their legal equivalents.

What is claimed is:

1. A device for analyzing one or more samples, the device comprising:
   a receptacle support configured to support a microplate comprising a microplate well configured to hold a sample;
   an incubation chamber configured to incubate the sample;
   an imaging subsystem configured to image the sample on a cell level from below the sample, wherein the imaging subsystem is disposed substantially below the incubation chamber;
   a non-imaging analyzing subsystem configured to analyze the sample on a well level, the non-imaging analyzing subsystem configured to provide at least one of a first measurement modality to measure an absorbance of the sample, a second measurement modality to measure fluorescence of the sample, and a third measurement modality to measure chemiluminescence of the sample;
   a positioning subsystem configured to position the receptacle support for the non-imaging analyzing subsystem to analyze the sample and the imaging subsystem to image the sample; and
   a temperature control subsystem configured to control temperature of an atmosphere around the sample to be different from a temperature of an atmosphere outside the device.

2. The device of claim 1, wherein the positioning subsystem is common to both the imaging subsystem and the non-imaging analyzing subsystem.

3. The device of claim 1, further comprising:
   a housing that forms an exterior of the device and that encloses the non-imaging analyzing subsystem, the imaging subsystem, the incubation chamber, and the positioning subsystem.

4. The device of claim 1, wherein the non-imaging analyzing subsystem is configured to provide the first measurement modality, the second measurement modality, and the third measurement modality.

5. The device of claim 1, wherein (i) one of the imaging subsystem and the non-imaging analyzing subsystem and (ii) the receptacle support share a commonly controlled atmospheric composition.

6. The device of claim 1, wherein the imaging subsystem, the non-imaging analyzing subsystem, and the receptacle support share a commonly controlled atmospheric composition.

7. The device of claim 1, wherein the imaging subsystem comprises an objective to image the sample.

8. The device of claim 1, wherein the imaging subsystem comprises a plurality of objectives mounted on a turret, the plurality of objectives mounted on the turret to be selectable to selectively image the sample.

9. The device of claim 1, wherein the imaging subsystem comprises an imaging light source, and
   wherein the non-imaging analyzing subsystem comprises at least one analyzing light source separate from the imaging light source.

10. The device of claim 1, further comprising:
a processor configured to control operations of the non-imaging analyzing subsystem and the imaging subsystem.

11. The device of claim 1, further comprising:
a user interface configured to receive a user input to control the operations of the non-imaging analyzing subsystem and the imaging subsystem.

12. The device of claim 1, wherein the non-analyzing subsystem comprises a monochromator, the monochromator having a tunable wavelength for tuning a measurement wavelength of the at least one of the first measurement modality, the second measurement modality, and the third measurement modality.

13. The device of claim 1, wherein a wavelength of the at least one of the first measurement modality, the second measurement modality, and the third measurement modality is continuously tunable.

14. The device of claim 1, further comprising:
a gas control subsystem configured to control a composition of the atmosphere around the sample to be different from a composition of the atmosphere outside the device.

15. The device of claim 14, wherein the composition of the atmosphere around the sample and the temperature of the atmosphere around the sample are conducive to cell viability.

16. The device of claim 14, further comprising:
a processor configured to control operations of the non-imaging analyzing subsystem, the imaging subsystem, the positioning subsystem, the temperature control subsystem, and the gas control subsystem.

17. The device of claim 16, further comprising:
a user interface configured to receive a user input to control the operations of the non-imaging analyzing subsystem, the imaging subsystem, the positioning subsystem, the temperature control subsystem, and the gas control subsystem.

18. A device for analyzing one or more samples, the device comprising:
a receptacle support configured to support a microplate comprising a microplate well configured to hold a sample;
an incubation chamber configured to incubate the sample;
an imaging subsystem configured to image the sample on a cell level from below the sample, wherein the imaging subsystem comprises an objective to image the sample and the imaging subsystem is disposed substantially below the incubation chamber;
a non-imaging analyzing subsystem configured to analyze the sample on a well level, the non-imaging analyzing subsystem configured to provide at least one of a first measurement modality to measure an absorbance of the sample, a second measurement modality to measure fluorescence of the sample, and a third measurement modality to measure chemiluminescence of the sample;
a positioning subsystem configured to position the receptacle support for the non-imaging analyzing subsystem to analyze the sample and the imaging subsystem to image the sample;
a temperature control subsystem configured to control temperature of an atmosphere around the sample to be different from a temperature of an atmosphere outside the device;
a gas control subsystem configured to control a composition of the atmosphere around the sample to be different from a composition of the atmosphere outside the device;
wherein the non-imaging analyzing subsystem comprises a monochromator, the monochromator having a tunable wavelength for tuning a measurement wavelength of the at least one of the first measurement modality, the second measurement modality, and the third measurement modality.

* * * * *